United States Patent
Hartwell et al.

(10) Patent No.: US 12,233,195 B2
(45) Date of Patent: Feb. 25, 2025

(54) NEGATIVE PRESSURE WOUND THERAPY APPARATUSES AND METHODS FOR USING THE SAME

(71) Applicant: T.J.Smith and Nephew,Limited, Hull (GB)

(72) Inventors: Edward Yerbury Hartwell, Hull (GB); Felix Clarence Quintanar, Hull (GB)

(73) Assignee: T.J.Smith and Nephew, Limited, Hull (GB)

(*) Notice: Subject to any disclaimer, the term of this patent is extended or adjusted under 35 U.S.C. 154(b) by 0 days.

(21) Appl. No.: 18/138,537

(22) Filed: Apr. 24, 2023

(65) Prior Publication Data
US 2023/0321335 A1 Oct. 12, 2023

Related U.S. Application Data

(63) Continuation of application No. 16/958,933, filed as application No. PCT/EP2018/085913 on Dec. 19, 2018, now Pat. No. 11,642,450.

(Continued)

(30) Foreign Application Priority Data

Aug. 15, 2018 (GB) .................................. 1813282.9

(51) Int. Cl.
*A61M 1/00* (2006.01)
(52) U.S. Cl.
CPC ................ *A61M 1/86* (2021.05); *A61M 1/74* (2021.05); *A61M 1/912* (2021.05); *A61M 1/913* (2021.05);

(Continued)

(58) Field of Classification Search
CPC .......... A61M 1/86; A61M 1/74; A61M 1/912; A61M 1/913; A61M 1/77; A61M 1/92;
(Continued)

(56) References Cited

U.S. PATENT DOCUMENTS

| D239,019 S | 3/1976 | Flinn |
|---|---|---|
| 4,328,828 A | 5/1982 | Cianci |

(Continued)

FOREIGN PATENT DOCUMENTS

| DE | 102015215165 A1 | 2/2017 |
|---|---|---|
| EP | 0883430 B1 | 1/2007 |

(Continued)

OTHER PUBLICATIONS

International Preliminary Report on Patentability for Application No. PCT/EP2018/085913, mailed on Jul. 9, 2020, 14 pages.

(Continued)

*Primary Examiner* — Philip R Wiest
*Assistant Examiner* — Brandon W. Levy
(74) *Attorney, Agent, or Firm* — Knobbe, Martens, Olson & Bear, LLP

(57) ABSTRACT

Embodiments of negative pressure wound therapy systems, apparatuses, and methods for operating the systems and apparatuses are disclosed. In some embodiments, a medical device is configured to detect an identity of a patient-contacting disposable connected to the medical device. The medical device automatically modifies one or more operational parameters of the medical device based on the identity of the patient-contacting disposable connected to the medical device. The medical device can include a user interface and modify automatically available selections in the user interface based on the identity of the patient-contacting disposable connected to the medical device.

9 Claims, 18 Drawing Sheets

Related U.S. Application Data

(60) Provisional application No. 62/612,263, filed on Dec. 29, 2017.

(52) U.S. Cl.
CPC .............. *A61M 1/77* (2021.05); *A61M 1/92* (2021.05); *A61M 1/94* (2021.05); *A61M 1/95* (2021.05); *A61M 1/96* (2021.05); *A61M 1/982* (2021.05); *A61M 2205/14* (2013.01); *A61M 2205/18* (2013.01); *A61M 2205/3344* (2013.01); *A61M 2205/3368* (2013.01); *A61M 2205/3553* (2013.01); *A61M 2205/3569* (2013.01); *A61M 2205/502* (2013.01); *A61M 2205/6018* (2013.01)

(58) Field of Classification Search
CPC ............ A61M 1/94; A61M 1/95; A61M 1/96; A61M 1/982; A61M 2205/14; A61M 2205/18; A61M 2205/3344; A61M 2205/3368; A61M 2205/3553; A61M 2205/3569; A61M 2205/502; A61M 2205/6018; A61M 1/918; A61M 2205/15; A61M 2205/3561; A61M 2205/60; A61M 1/90; A61M 1/80; A61M 2039/1044; A61M 2205/3334; A61M 2205/6054; A61M 1/882; A61M 1/0058; A61M 2205/581; A61M 39/10; A61M 2205/6072; A61M 2205/52; A61M 2205/50; A61M 2230/005; A61M 16/024; A61M 2005/1726; A61M 2205/3331; A61M 16/0051; A61M 2205/3546; A61M 16/0003; A61M 2205/3576; A61M 16/0816; A61M 27/00; A61F 13/00068; A61F 2013/00174; A61F 2013/00536; A61F 2013/00089; A61F 13/0216; G16H 40/67; G16H 10/60; G16H 40/40; G16H 50/20; G16H 20/13; G16H 20/10; G06F 3/04847; F04B 43/09; F04B 49/065; F04B 45/047; F04B 49/06; F04B 43/0081; F04B 49/00

See application file for complete search history.

(56) References Cited

U.S. PATENT DOCUMENTS

| | | |
|---|---|---|
| 4,498,850 A | 2/1985 | Perlov et al. |
| 4,731,076 A | 3/1988 | Noon et al. |
| D357,735 S | 4/1995 | McPhee |
| 5,514,088 A | 5/1996 | Zakko |
| 5,712,795 A | 1/1998 | Layman et al. |
| 6,027,490 A | 2/2000 | Radford et al. |
| 6,203,291 B1 | 3/2001 | Stemme et al. |
| 6,232,680 B1 | 5/2001 | Bae et al. |
| 6,396,407 B1 | 5/2002 | Kobayashi |
| D475,132 S | 5/2003 | Randolph |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,214,202 B1 | 5/2007 | Vogel et al. |
| D581,042 S | 11/2008 | Randolph et al. |
| D590,934 S | 4/2009 | Randolph et al. |
| D602,582 S | 10/2009 | Pidgeon et al. |
| D602,583 S | 10/2009 | Pidgeon et al. |
| D602,584 S | 10/2009 | Pidgeon et al. |
| 7,608,066 B2 | 10/2009 | Vogel |
| 7,611,500 B1 | 11/2009 | Lina et al. |
| 7,857,806 B2 | 12/2010 | Karpowicz et al. |
| 7,927,319 B2 | 4/2011 | Lawhorn |
| D645,137 S | 9/2011 | Gonzalez |
| 8,021,348 B2 | 9/2011 | Risk, Jr. et al. |
| 8,062,272 B2 | 11/2011 | Weston |
| 8,066,243 B2 | 11/2011 | Svedman et al. |
| 8,070,735 B2 | 12/2011 | Koch et al. |
| D654,164 S | 2/2012 | Cole et al. |
| D660,409 S | 5/2012 | Taggerty et al. |
| 8,215,929 B2 | 7/2012 | Shen et al. |
| 8,216,197 B2 | 7/2012 | Simmons et al. |
| 8,226,620 B2 | 7/2012 | Giezendanner et al. |
| 8,308,714 B2 | 11/2012 | Weston et al. |
| 8,317,774 B2 | 11/2012 | Adahan |
| 8,366,692 B2 | 2/2013 | Weston et al. |
| 8,409,160 B2 | 4/2013 | Locke et al. |
| 8,480,641 B2 | 7/2013 | Jacobs |
| 8,540,688 B2 | 9/2013 | Eckstein et al. |
| 8,641,693 B2 | 2/2014 | Locke et al. |
| 8,668,677 B2 | 3/2014 | Eckstein et al. |
| 8,858,517 B2 | 10/2014 | Pan et al. |
| 8,905,985 B2 | 12/2014 | Allen et al. |
| 9,050,398 B2 | 6/2015 | Armstrong et al. |
| 9,084,845 B2 | 7/2015 | Adie et al. |
| 9,138,531 B2 | 9/2015 | Yodfat et al. |
| 9,199,010 B2 | 12/2015 | Yao et al. |
| D750,222 S | 2/2016 | Chang |
| D750,235 S | 2/2016 | Maurice |
| D750,236 S | 2/2016 | Maurice |
| D757,260 S | 5/2016 | Lombardi, III et al. |
| 9,327,063 B2 | 5/2016 | Locke et al. |
| 9,333,281 B2 | 5/2016 | Giezendanner et al. |
| D764,047 S | 8/2016 | Bjelovuk et al. |
| D764,048 S | 8/2016 | Bjelovuk et al. |
| D764,653 S | 8/2016 | Bjelovuk et al. |
| D764,654 S | 8/2016 | Bjelovuk et al. |
| 9,415,199 B2 | 8/2016 | Tsai |
| 9,427,505 B2 | 8/2016 | Askem et al. |
| D765,830 S | 9/2016 | Bjelovuk et al. |
| 9,445,948 B2 | 9/2016 | Smola |
| D773,658 S | 12/2016 | Bow |
| 9,586,036 B2 | 3/2017 | Masuda et al. |
| D788,293 S | 5/2017 | Eckstein et al. |
| D791,939 S | 7/2017 | Turturro et al. |
| D792,586 S | 7/2017 | Becker |
| 9,737,649 B2 | 8/2017 | Begin et al. |
| D797,275 S | 9/2017 | Evans et al. |
| 9,901,664 B2 | 2/2018 | Askem |
| 9,923,401 B2 | 3/2018 | Jung |
| 10,124,093 B1 | 11/2018 | Francis et al. |
| 10,143,785 B2 | 12/2018 | Adams et al. |
| 10,155,070 B2 | 12/2018 | Childress et al. |
| D842,460 S | 3/2019 | Gierse et al. |
| D851,759 S | 6/2019 | Jones et al. |
| D852,356 S | 6/2019 | Steele et al. |
| D888,225 S | 6/2020 | Askem |
| 2002/0013545 A1 | 1/2002 | Soltanpour et al. |
| 2002/0030002 A1* | 3/2002 | Verkaart .............. B01D 36/001 210/94 |
| 2002/0098097 A1 | 7/2002 | Singh |
| 2002/0161317 A1 | 10/2002 | Risk et al. |
| 2004/0068224 A1 | 4/2004 | Couvillon, Jr. et al. |
| 2005/0234485 A1 | 10/2005 | Seegert et al. |
| 2006/0281398 A1 | 12/2006 | Yokomizo et al. |
| 2008/0005000 A1* | 1/2008 | Radl ...................... G07F 17/06 705/34 |
| 2008/0234641 A1 | 9/2008 | Locke et al. |
| 2009/0216205 A1 | 8/2009 | Ryan et al. |
| 2009/0299306 A1 | 12/2009 | Buan |
| 2010/0022990 A1 | 1/2010 | Karpowicz et al. |
| 2010/0155465 A1* | 6/2010 | Mollstam ............ G06K 19/041 235/487 |
| 2010/0244780 A1 | 9/2010 | Turner et al. |
| 2011/0006876 A1 | 1/2011 | Moberg et al. |
| 2011/0060300 A1 | 3/2011 | Weig et al. |
| 2011/0076170 A1 | 3/2011 | Fujisaki et al. |
| 2011/0196291 A1 | 8/2011 | Vischer et al. |
| 2012/0078181 A1 | 3/2012 | Smith et al. |
| 2012/0109083 A1 | 5/2012 | Coulthard et al. |
| 2012/0289913 A1 | 11/2012 | Eckstein et al. |
| 2013/0012772 A1 | 1/2013 | Gunday et al. |
| 2013/0025692 A1 | 1/2013 | Heide et al. |

(56) References Cited

U.S. PATENT DOCUMENTS

| | | |
|---|---|---|
| 2013/0053795 A1 | 2/2013 | Coulthard et al. |
| 2013/0131616 A1 | 5/2013 | Locke |
| 2013/0237937 A1 | 9/2013 | Ramella et al. |
| 2013/0270166 A1 | 10/2013 | Locke et al. |
| 2013/0274718 A1 | 10/2013 | Yao et al. |
| 2014/0023533 A1 | 1/2014 | Ishii et al. |
| 2014/0276488 A1 | 9/2014 | Locke et al. |
| 2015/0174320 A1 | 6/2015 | Grant et al. |
| 2015/0231021 A1 | 8/2015 | Smith et al. |
| 2015/0246164 A1 | 9/2015 | Heaton et al. |
| 2015/0320916 A1 | 11/2015 | Croteau et al. |
| 2016/0015872 A1 | 1/2016 | Luckemeyer et al. |
| 2016/0015957 A1 | 1/2016 | Tieck et al. |
| 2016/0101278 A1 | 4/2016 | Norris et al. |
| 2016/0213843 A1 | 7/2016 | Despa et al. |
| 2016/0250398 A1 | 9/2016 | Barr et al. |
| 2016/0271305 A1 | 9/2016 | Kurihara et al. |
| 2016/0303358 A1 | 10/2016 | Croizat et al. |
| 2017/0165405 A1 | 6/2017 | Muser et al. |
| 2017/0189588 A1 | 7/2017 | Croizat et al. |
| 2017/0189666 A1 | 7/2017 | Sealfon et al. |
| 2017/0224975 A1* | 8/2017 | Peer ........................ A61M 39/10 |
| 2017/0296716 A1 | 10/2017 | Middleton et al. |
| 2017/0319758 A1 | 11/2017 | Eddy et al. |
| 2017/0354767 A1 | 12/2017 | Carr et al. |
| 2018/0001000 A1 | 1/2018 | Herwig et al. |
| 2018/0021178 A1 | 1/2018 | Locke et al. |
| 2018/0104391 A1 | 4/2018 | Luxon et al. |
| 2018/0140466 A1 | 5/2018 | Hunt |
| 2018/0250459 A1 | 9/2018 | Kimball et al. |
| 2018/0318476 A1 | 11/2018 | Askem et al. |
| 2019/0021541 A1 | 1/2019 | Kuempel |
| 2019/0192744 A1 | 6/2019 | Greener et al. |
| 2019/0358372 A1 | 11/2019 | Askem et al. |
| 2020/0121833 A9 | 4/2020 | Askem et al. |
| 2021/0077670 A1 | 3/2021 | Long et al. |
| 2021/0392761 A1 | 12/2021 | Kitagawa et al. |

FOREIGN PATENT DOCUMENTS

| | | | |
|---|---|---|---|
| EP | 2255837 A1 | 12/2010 | |
| EP | 3124059 A1 | 2/2017 | |
| EP | 3124060 A1 | 2/2017 | |
| FR | 2939320 A1 | 6/2010 | |
| GB | 1220857 A | 1/1971 | |
| JP | S5647279 U | 4/1981 | |
| JP | H01101978 A | 4/1989 | |
| JP | H0796029 A | 4/1995 | |
| JP | 2007218241 A | 8/2007 | |
| JP | 6047279 B2 | 12/2016 | |
| WO | WO-0061206 A1 | 10/2000 | |
| WO | WO-03081762 A1 | 10/2003 | |
| WO | WO-03101508 A2 | 12/2003 | |
| WO | WO-2008033788 A2 | 3/2008 | |
| WO | WO-2009071924 A1 | 6/2009 | |
| WO | WO-2011075706 A1 | 6/2011 | |
| WO | WO-2011094410 A2 | 8/2011 | |
| WO | WO-2012004298 A1 | 1/2012 | |
| WO | WO-2012100624 A1 | 8/2012 | |
| WO | WO-2013015827 A2 | 1/2013 | |
| WO | WO-2013064852 A1 | 5/2013 | |
| WO | WO-2013078214 A1 | 5/2013 | |
| WO | WO-2013171585 A2 * | 11/2013 | ........ A61F 13/00068 |
| WO | WO-2014115819 A1 | 7/2014 | |
| WO | WO-2014164655 A1 | 10/2014 | |
| WO | WO-2015197462 A1 | 12/2015 | |
| WO | WO-2016018448 A1 * | 2/2016 | ........ A61F 13/00068 |
| WO | WO-2016103031 A1 | 6/2016 | |
| WO | WO-2016109048 A1 | 7/2016 | |
| WO | WO-2017044138 A1 | 3/2017 | |
| WO | WO-2017062042 A1 | 4/2017 | |
| WO | WO-2017160412 A1 | 9/2017 | |
| WO | WO-2017197357 A4 | 1/2018 | |
| WO | WO-2018009873 A1 | 1/2018 | |
| WO | WO-2018009880 A1 | 1/2018 | |
| WO | WO-2018041854 A1 | 3/2018 | |
| WO | WO-2018150263 A1 | 8/2018 | |
| WO | WO-2018150267 A2 | 8/2018 | |
| WO | WO-2018167199 A1 | 9/2018 | |
| WO | WO-2018185101 A1 | 10/2018 | |
| WO | WO-2018195101 A1 | 10/2018 | |
| WO | WO-2019063467 A1 | 4/2019 | |
| WO | WO-2019129581 A2 | 7/2019 | |
| WO | WO-2019139829 A1 | 7/2019 | |
| WO | WO-2019179943 A1 | 9/2019 | |
| WO | WO-2019211730 A1 | 11/2019 | |
| WO | WO-2019211731 A1 | 11/2019 | |
| WO | WO-2019211732 A1 | 11/2019 | |
| WO | WO-2019224059 A1 | 11/2019 | |
| WO | WO-2020011690 A1 | 1/2020 | |

OTHER PUBLICATIONS

International Search Report and Written Opinion for Application No. PCT/EP2018/085913, mailed on Jul. 29, 2019, 20 pages.

Invitation to Pay Additional Fees and Partial Search Report for Application No. PCT/EP2018/085913, mailed on Apr. 24, 2019, 17 pages.

Jenkins R.W., et al., "Mechanisms of Resistance to Immune Checkpoint Inhibitors," British Journal of Cancer, Jan. 2, 2018, vol. 118, https://doi.org/10.1038/bjc.2017.434 , pp. 9-16.

Search Report under Section 17(5) mailed Feb. 7, 2019 for Great Britain Application No. 1813282.9, 5 pages.

Wikipedia, "Battery Charger," retrieved from https://web.archive.org/web/20181109005000/https://en.wikipedia.org/wiki/Battery_charger , on Nov. 9, 2018, 12 pages.

* cited by examiner

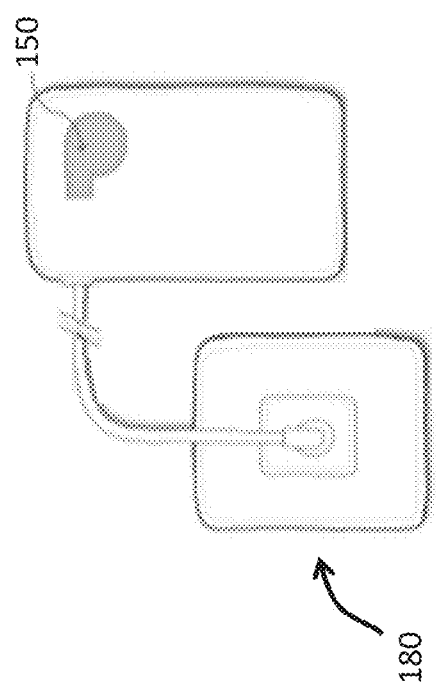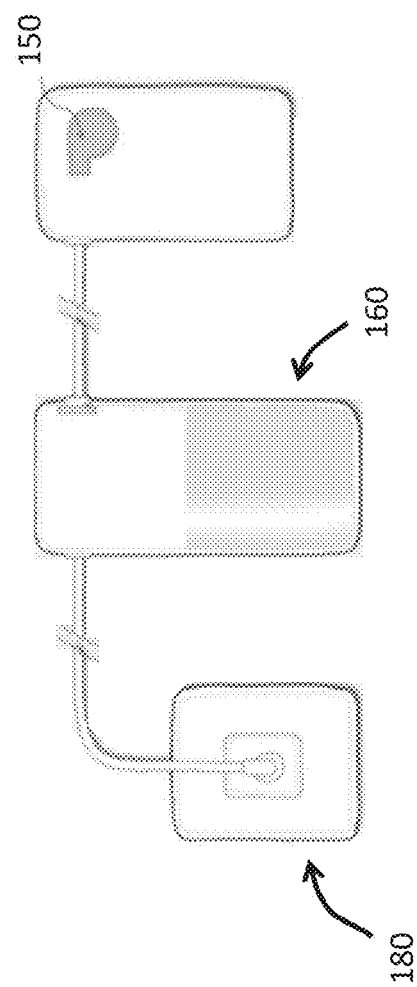

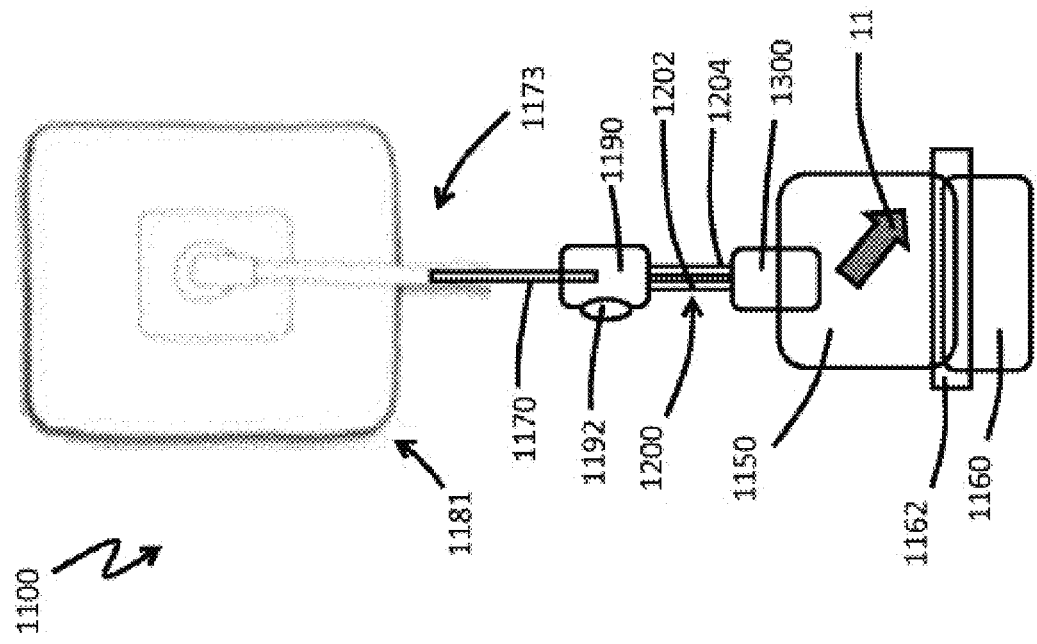
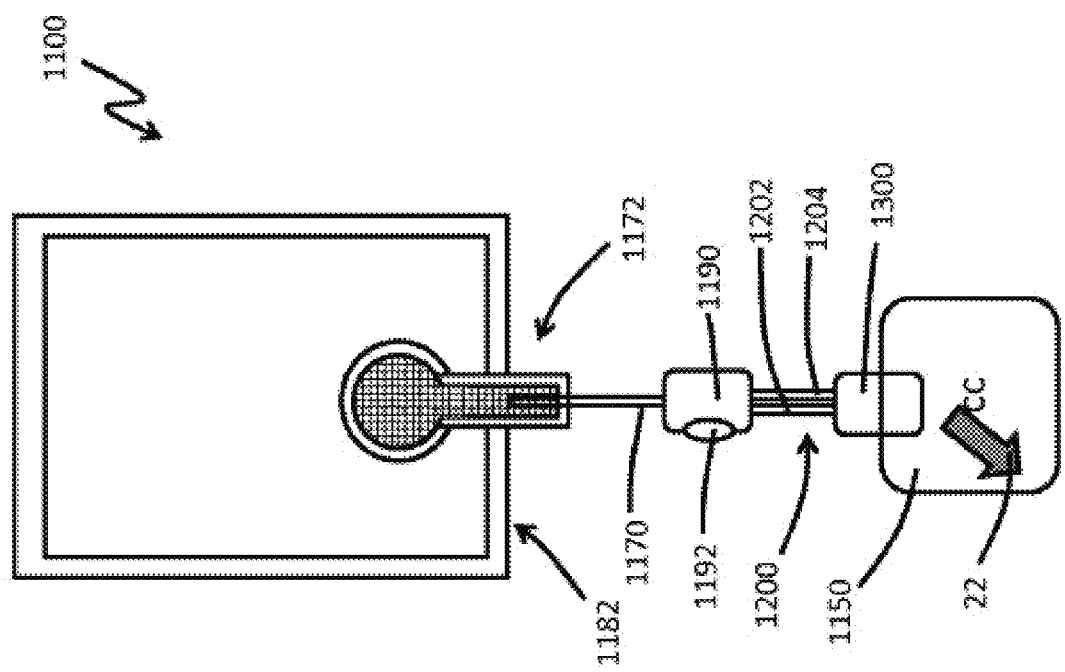

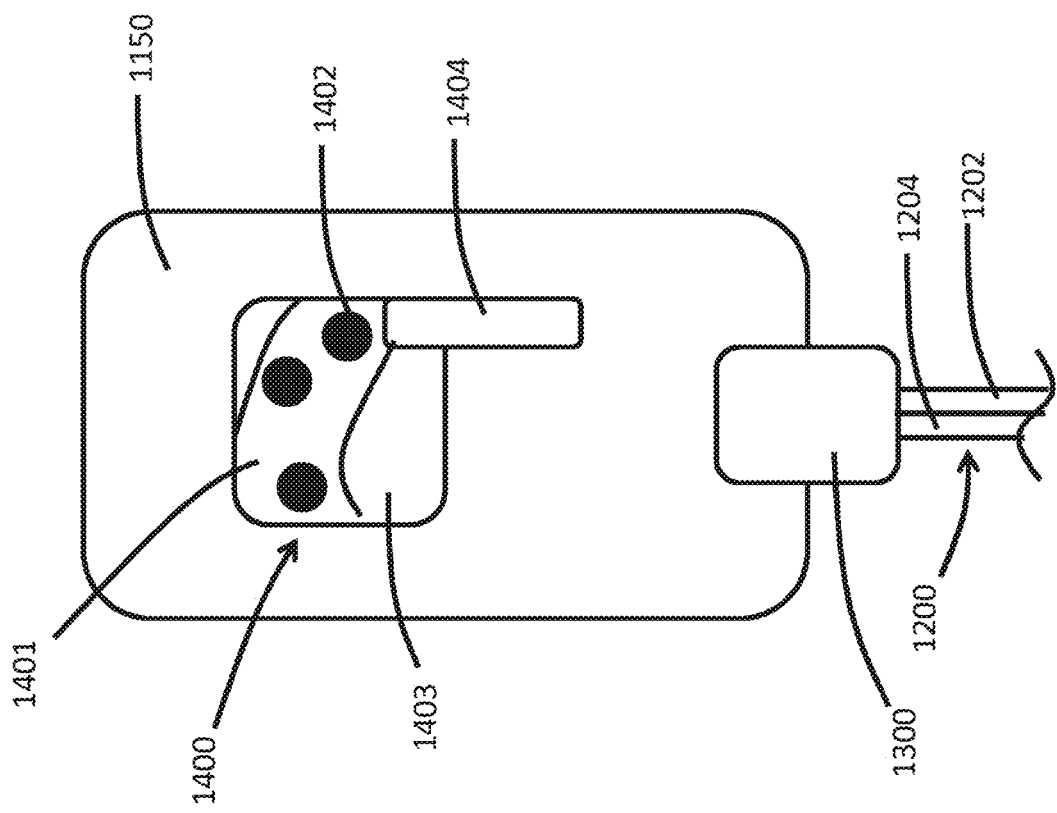

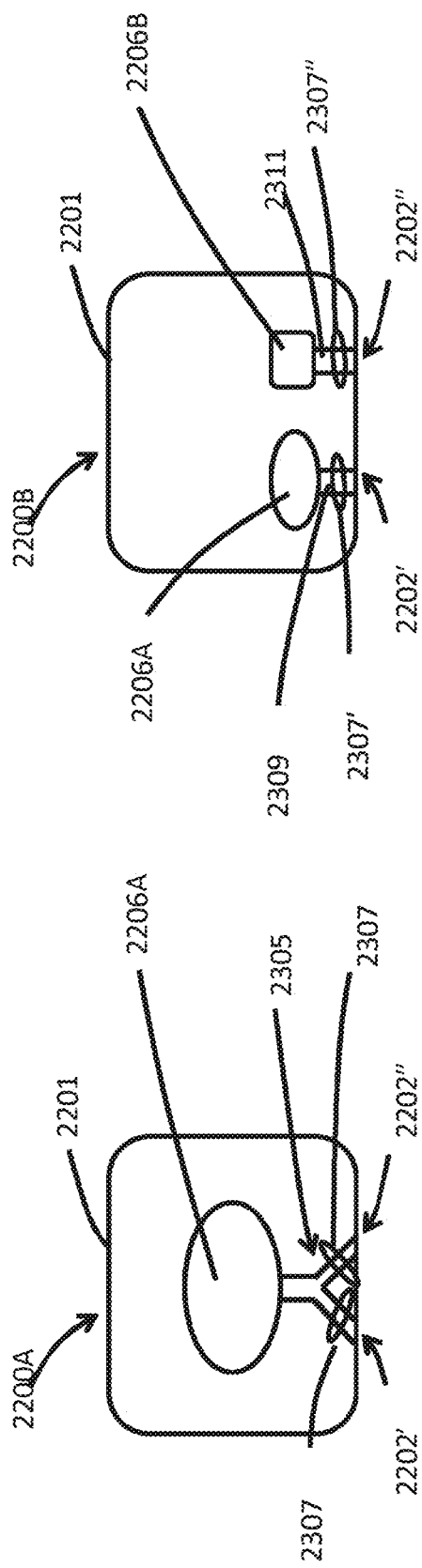

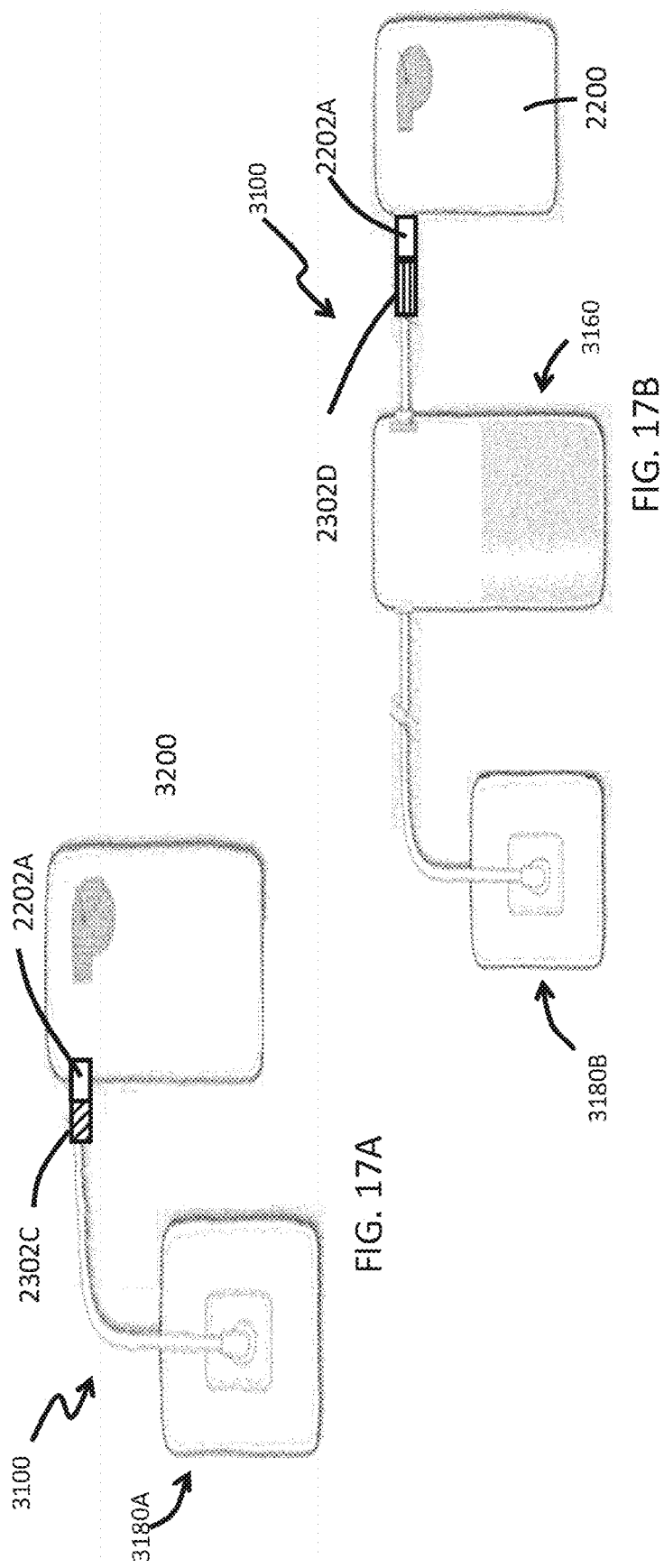

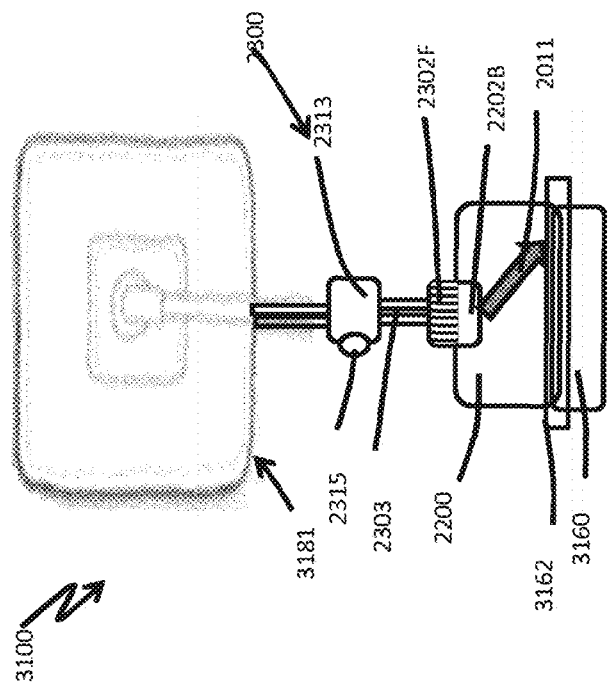
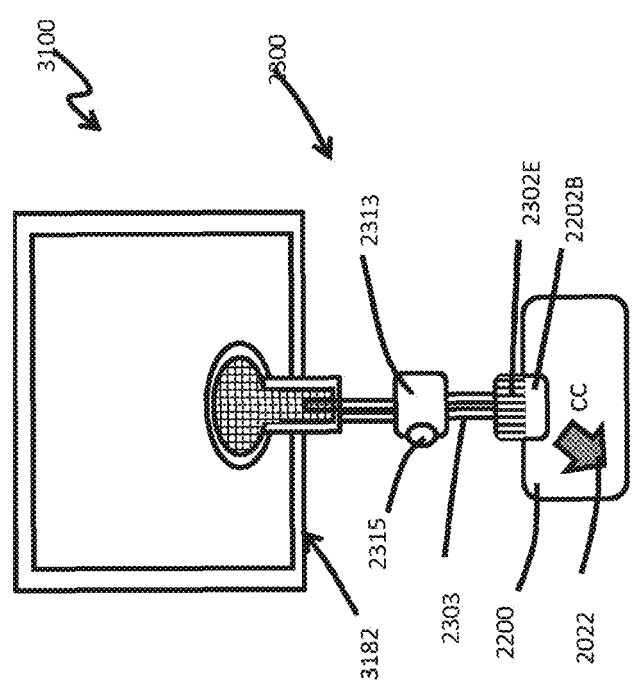

NEGATIVE PRESSURE WOUND THERAPY APPARATUSES AND METHODS FOR USING THE SAME

RELATED APPLICATIONS

This application is a continuation of U.S. application Ser. No. 16/958,933, filed Jun. 29, 2020, which is a U.S. national stage application of International Patent Application No. PCT/EP2018/085913, filed Dec. 19, 2018, which claims priority to Great Britain Patent Application Number 1813282.9, filed Aug. 15, 2018, and entitled "SYSTEM FOR MEDICAL DEVICE ACTIVATION AND OPERATION," and claims priority to U.S. Provisional Patent Application 62/612,263, filed Dec. 29, 2017, and entitled "NEGATIVE PRESSURE WOUND THERAPY APPARATUSES AND METHODS FOR USING THE SAME," the entirety of each of which applications is hereby incorporated by reference.

BACKGROUND

Embodiments or arrangements disclosed herein relate to methods and apparatuses for dressing and treating a wound with topical negative pressure (TNP) therapy. For example, but without limitation, any embodiments disclosed herein may relate to treating a wound with reduced pressure provided from a pump kit. Although not required, any embodiments of the pump kit can be sterile. As another non-limiting example, any embodiments disclosed herein relate to apparatuses and methods for controlling the operation of a TNP system. In some aspects, this disclosure generally relates to systems, methods, and devices for activating or controlling a medical device, in particular, for activating or controlling a pump assembly of a negative pressure wound therapy system.

Many different types of wound dressings are known for aiding in the healing process of a human or animal. These different types of wound dressings include many different types of materials and layers, for example, pads such as gauze pads or foam pads. Topical negative pressure ("TNP") therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue edema; encouraging blood flow; stimulating the formation of granulation tissue; removing excess exudates, and may reduce bacterial load and thus reduce the potential for infection of the wound. Furthermore, TNP therapy permits less outside disturbance of the wound and promotes more rapid healing. A medical device (e.g., a TNP therapy device) can include a user interface that allows a user to set or control the operation of the medical device. The user interface can be complex, making it difficult for a user to select the correct settings for the operation of the medical device. A need exists for simplifying the process by which a user sets or controls the operation of a medical device.

SUMMARY

Embodiments of the present disclosure relate to apparatuses and methods for wound treatment. Some of the wound treatment apparatuses described herein comprise a pump system or assembly for providing negative pressure to a wound site. Wound treatment apparatuses may also comprise wound dressings that may be used in combination with the pump assemblies described herein, and connectors for connecting the wound dressings to the pump assemblies.

Some of the embodiments described herein provide a negative pressure wound therapy system. The system may comprise a pump assembly that is adaptable for use in a canister mode and in a canisterless mode. In the canister mode, the pump assembly can provide negative pressure to a canister-mode wound dressing and direct wound exudate from the wound to a collection canister. In the canisterless mode, the pump assembly can provide negative pressure to a canisterless-mode wound dressing that includes one or more absorbent layers to collect wound exudate within the canisterless-mode wound dressing without using a separate canister.

The system of the preceding paragraph can further include one or more of the following features: The system can include the canister-mode wound dressing. The canister-mode wound dressing can include a foam layer and a backing layer. The system can include the canisterless-mode wound dressing. The canisterless-mode wound dressing can include a filter to retain wound exudate within the wound dressing. The canisterless-mode wound dressing can include a wound contact layer underneath the one or more absorbent layers. The canisterless-mode wound dressing can include a transmission layer above the one or more absorbent layers. A thermoplastic spun lace layer can be disposed between the transmission layer and the one or more absorbent layers. The system can include a collection canister configured to be used with the canister-mode dressing. The pump assembly can be configured to be removably attached to the collection canister. The system can be configured so that a flow of gas travels through the pump assembly along a first flowpath when the pump assembly is used in the canister mode and along a second flowpath when the pump assembly is used in canisterless mode. Connecting a canister to the pump assembly can cause the flow of gas to switch to the first flowpath from the second flowpath. The system can include a connector adapter disposed upstream of an inlet of the pump assembly. The system can include a proximal conduit configured to connect the connector adapter to the inlet of the pump assembly and/or a distal conduit configured to connect the connector adapter to a wound dressing disposed upstream of the connector adapter. One or more of the proximal or distal conduits can include a dual lumen conduit. A first lumen of the dual lumen conduit can be connected to a first pressure sensor configured to measure pressure at a first location in a flowpath fluidically connecting the pump assembly to a wound. The second lumen of the dual lumen conduit can be connected to a second pressure sensor at a second location in the flowpath downstream of the first location. The system can include a controller configured to receive and determine a difference between pressure measurements from the first and second pressure sensors and, based on the difference, determine and indicate one or more of blockage in the flowpath, leak in the flowpath, or canister full conditions. The first lumen of the dual lumen conduit can be connected to a bleed valve. The system can include a controller configured to operate the bleed valve to allow atmospheric air to enter a flowpath fluidically connecting the pump assembly to a wound. The pump assembly can be configured to operate in canister mode when the pump is seated onto a canister. The pump assembly can be blocked from being seated onto a canister when the pump assembly is connected to a canisterless-mode dressing. The system can include a controller configured to provide a first set of alarms, pump controls, and/or menu selections when the pump assembly operates in the canister mode and a second set of alarms, pump controls, and/or menu selections when the pump assembly operates in the canisterless mode, the first set being different from the second set. The system can include a controller configured to pause operation of the pump assembly but not shut down the pump assembly in response to a selection of an inactive mode. The controller can be configured to shut down the pump assembly in response to operation in the inactive mode exceeding a time duration.

Some of the embodiments described herein provide a negative pressure wound therapy kit. The kit includes a pump assembly, a wound dressing, and a conduit. The pump assembly is configured to be used in a canister mode and in a canisterless mode. The conduit is adapted to connect the wound dressing to the pump assembly.

The kit of the preceding paragraph can further include one or more of the following features: The wound dressing is packaged separately from the pump assembly. The wound dressing is packaged together with the conduit. The wound dressing comprises a backing layer and a wound filler. The kit includes a canister. The wound dressing includes a backing layer, a wound contact layer, and an absorbent layer. The kit includes a first wound dressing and a second wound dressing, wherein the first wound dressing comprises a backing layer and a wound filler and the second wound dressing comprises a backing layer, a wound contact layer, and an absorbent layer. The kit includes a flexible conduit comprising a monofilament yarn for connecting the wound dressing to the pump assembly.

Some of the embodiments described herein provide a negative pressure system for use by a single patient. This system may comprise a pump assembly that is adaptable for use with and without a separate wound exudate collection canister and for use with different dressing types depending on whether a separate wound exudate collection canister is used. The pump assembly may be configured to detect whether a dressing with or without a separate collection canister is used. In some embodiments, different types of connectors may be utilized to connect to the pump unit, and the pump assembly may be configured to determine a desired mode of operation based on the type of connector used.

Embodiments of the present disclosure relate to apparatuses and methods for controlling or activating a medical device. In certain aspects, the systems of the present disclosure include a patient-contacting disposable that communicates with the medical device upon connection of the patient-contacting disposable with the medical device. In certain arrangements, the medical device is a pump assembly of a negative pressure wound therapy (NPWT) system. In some variants, the patient-contacting disposable is a wound dressing. In some embodiments, the system includes a wound dressing that activates or powers on the pump assembly of the NPWT system when the wound dressing is connected to the pump assembly.

In some embodiments, a negative pressure wound therapy system is disclosed. The system includes a pump assembly and a connector port disposed on the pump assembly. The connector port is adapted to receive a connector associated with a component of a wound dressing. The connector port is further configured such that connection of the connector to the connector port informs the pump assembly of one or more characteristics of the component of the wound dressing that is associated with the connector that is connected to the connector port. The pump assembly is configured to automatically adjust an operational parameter of the pump assembly based on the one or more characteristics of the component of the wound dressing that is associated with the connector that is connected to the connector port.

In some embodiments, a negative pressure wound therapy system is disclosed that includes a negative pressure source, a first connector port, a second connector port, and a Y-connect feature. The negative pressure source is disposed within a housing, and the first and second connector ports are disposed on or attached to the housing. The first connector port is configured to receive a first connector associated with a component of a first wound dressing. The second connector port is configured to receive a second connector associated with a component of a second wound dressing. The Y-connect feature fluidically connects the negative pressure source to each of the first and second connector ports. In some embodiments, the Y-connect feature is integrally formed with the first connector port and the second connector port as a single piece. The system is configured such that connection of the first connector to the first connector port informs the negative pressure wound therapy system of one or more characteristics of the component of the wound dressing that is associated with the first connector. The system may also be configured such that connection of the second connector to the second connector port informs the negative pressure wound therapy system of one or more characteristics of the component of the wound dressing that is associated with the second connector. The negative pressure wound therapy system is configured to automatically adjust an operational parameter of the negative pressure source based on the one or more characteristics of the component(s) of the wound dressing(s) that is associated with the first connector that is connected to the first connector port and/or the second connector that is connected to the second connector port. In some embodiments, alarms may be adjusted based on the system being informed of the one or more characteristics of any of the components connected to the first and/or second connector ports.

In some embodiments, a negative pressure wound therapy system is disclosed that includes a negative pressure source, an irrigation source, a first connector port, and a second connector port. The negative pressure source and the irrigation source are disposed within a housing. The first and second connector ports are disposed on the housing. The first connector port is configured to receive a first connector associated with a wound dressing. The first connector port is connected to the negative pressure source by a first flow path. The first connector port is configured such that connection of the first connector to the first connector port informs the negative pressure wound therapy system that the first connector is attached to the first connector port. The second connector port is configured to receive a second connector associated with the wound dressing. The second connector port is connected to the irrigation source by a second flow path. The second connector port is configured such that connection of the second connector to the second connector port informs the negative pressure wound therapy system that the second connector is attached to the second connector port. The negative pressure source and the irrigation source are each configured to power on only when the first connector is connected to the first connector port and the second connector is connected to the second connector port.

Embodiments or arrangements of the present disclosure are described for illustrative purposes in the context of methods and systems for treating a wound with topical negative pressure (TNP) therapy. However, the present disclosure is not limited to medical devices that are used for TNP therapy and can be applied to medical devices other than medical devices that are used for TNP therapy. The present disclosure can be implemented, for example, in the context of blood glucose monitoring devices, dialysis machines, or other medical devices.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

Embodiments of the present disclosure will now be described hereinafter, by way of example only, with reference to the accompanying drawings in which:

FIG. 2A illustrates a reduced pressure wound therapy system operating in a canisterless mode of operation.

FIG. 2B illustrates a reduced pressure wound therapy system operating in a canister mode of operation.

FIG. 5A illustrates a TNP system with a canisterless-mode dressing according to some embodiments.

FIG. 5B illustrates a TNP system with a canister-mode dressing according to some embodiments.

FIG. 10 illustrates a back view of the pump assembly of FIG. 9.

FIG. 15B illustrates a schematic diagram of a system for automating activation or operation of a medical device according to some embodiments.

FIG. 15C illustrates a schematic diagram of a system for automating activation or operation of a medical device according to some embodiments.

FIG. 17A illustrates a negative pressure wound therapy system connected to a canisterless wound dressing.

FIG. 17B illustrates a negative pressure wound therapy system connected to a canister and a canister-mode dressing.

FIG. 18A illustrates a negative pressure wound therapy system connected to a canisterless wound dressing.

FIG. 18B illustrates a negative pressure wound therapy system connected to a canister and a canister-mode dressing.

DETAILED DESCRIPTION

Overview

Figure 1:
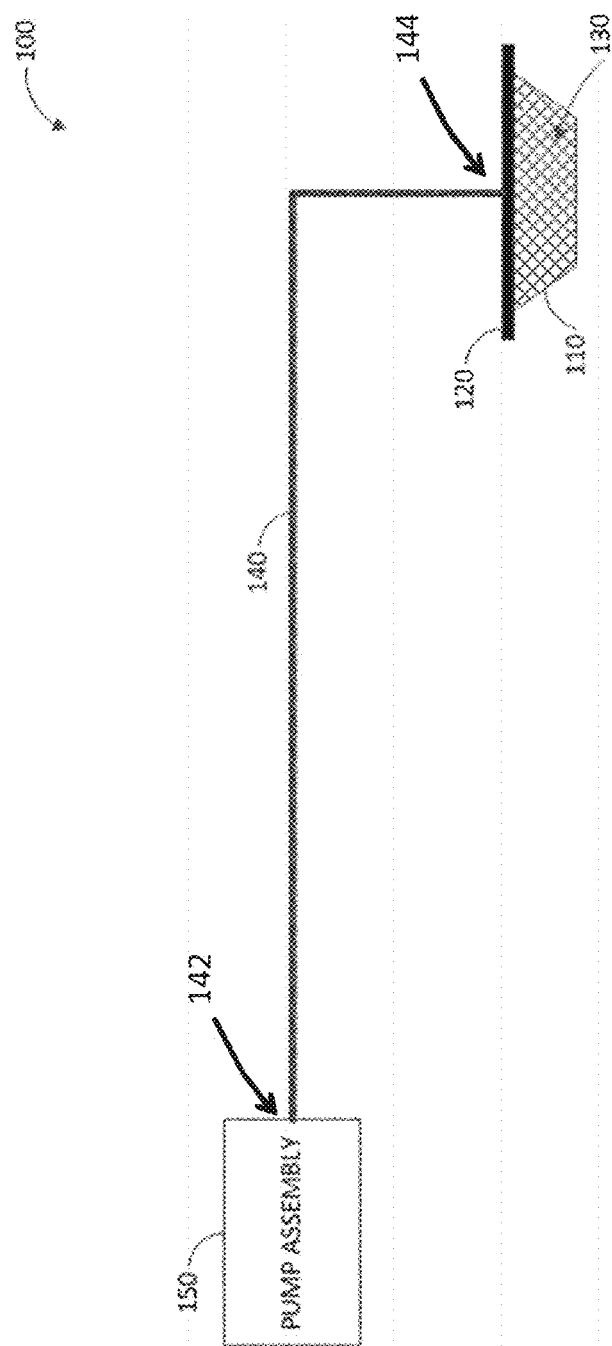
FIG. 1 illustrates a reduced pressure wound therapy system including a pump assembly according to some embodiments.

Embodiments disclosed herein relate to systems and methods of treating a wound with reduced pressure. As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below, for example, 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is farther from atmospheric pressure (e.g., −80 mmHg is more than ~60 mmHg). In some embodiments, local ambient atmospheric pressure is used as a reference point, and such local atmospheric pressure may not necessarily be, for example, 760 mmHg.

Embodiments of the present disclosure are generally applicable to use in topical negative pressure (TNP) or reduced pressure therapy systems. Briefly, negative pressure wound therapy assists in the closure and healing of many forms of "hard to heal" wounds by reducing tissue edema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

As discussed above, activation of an electrical medical device and prescription of a therapy regime delivered by the device can be complex for a user to set or program into the device. The device can have a user interface with multiple options and indications for the user to select. For example, a pump assembly of a negative pressure wound therapy (NPWT) system can allow a user to select multiple therapy options such as the wound pressure, the temporal variation of wound pressure intensity, the volume of fluid infused into the wound, the pressure of the fluid infused into the wound, the time of therapy, and other operational parameters of the pump assembly. Medical devices other than NPWT pump assemblies also have operational parameters that are complex for a user to set or program into the device. For the sake of clarity, the systems and methods of the present disclosure are described herein often in terms of NPWT systems. However, the present disclosure is not limited to NPWT medical devices and can be applied to the activation and operation of medical devices in general.

Negative Pressure System

FIG. 1 illustrates an embodiment of a negative or reduced pressure wound treatment (or TNP) system 100 comprising a wound filler 130 placed inside a wound cavity 110, the wound cavity 110 sealed by a wound cover 120. In some embodiments, one or more of the wound filler 130, the wound cover 120, or any other component, such as a contact layer (not shown), make up a wound dressing. The system 100 includes a negative pressure wound therapy apparatus or a pump assembly 150 configured to provide reduced pressure to the wound. For example, a conduit 140 having at least one lumen can provide a fluid flow path between the pump assembly 150 and the wound. The conduit 140 can have a pump end 142 that is fluidically connected to the pump assembly 150 and a wound end 144 that is inserted under or through the wound cover 120. The conduit 140 can communicate a negative pressure at the pump end 142 to the wound end 144.

FIGS. 2A-2B illustrate that the reduced pressure wound therapy system can be configured to operate with and without a canister (e.g., canister and canisterless modes). In particular, the same pump assembly 150 described can be used in both canister and canisterless modes. FIG. 2A shows an embodiment of the TNP system 100 that has a wound dressing 180 connected directly to the pump assembly 150 (e.g., canisterless mode). FIG. 2B shows an embodiment of the TNP system 100 that has a canister 160 interposed between a wound dressing 180 and the pump assembly 150 (e.g., canister mode). At the beginning of the application of negative pressure wound therapy to a wound when the wound is in the early stages of the healing process and exudes a significant volume of exudate, the reduced pressure wound therapy system may operate with a canister. In this mode of operation, the negative pressure wound therapy system may operate with a foam or gauze RENASYS™ dressing sold by Smith & Nephew or any other suitable dressing. Operation of the reduced pressure wound therapy system with a canister may sometimes be referred to herein as "RENASYS™", "RENASYS™-mode", or derivatives thereof. As the wound is progressing through the healing process and is starting to exude a smaller volume of exudate, the canister may be removed and the negative pressure wound therapy system may operate with an absorbent dressing, such as the PICO™ dressing sold by Smith & Nephew or any other suitable dressing that retains the wound exudate within the dressing. Further details of absorbent dressings such as the PICO™ dressing are found in U.S. Pat. No. 9,061,095, filed on Apr. 21, 2011, and incorporated in its entirety by reference herein. Operation of the reduced pressure wound therapy system without a canister may sometimes be referred to herein as PICO™, "PICO™-mode", or derivatives thereof.

Pump Assembly

Figure 3A:
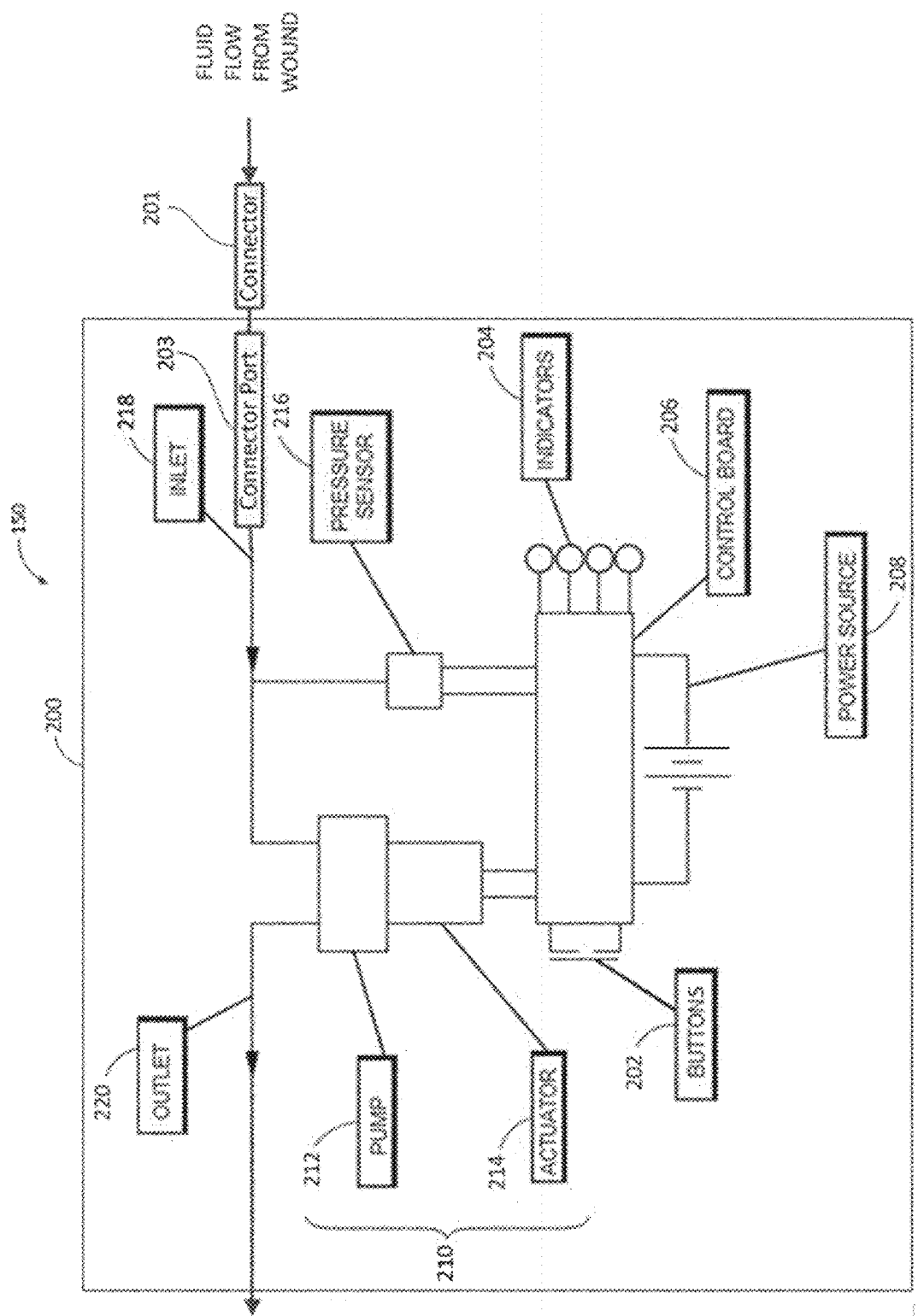
FIGS. 3A-3B illustrates a schematic of a reduced pressure wound therapy system including a pump assembly according to some embodiments.

FIG. 3A illustrates a schematic of the pump assembly 150 according to some embodiments. The pump assembly 150 can include a housing 200 that encloses or supports at least some components of the pump assembly 150. The pump assembly 150 can include one or more switches or buttons 202, one or more indicators 204, and a control board 206. The one or more buttons 202 and the one or more indicators 204 (which collectively make up a user interface) can be in electrical communication with the control board 206, which can include one or more controllers and memory. The one or more buttons 202 can be used for any suitable purpose for controlling an operation of the pump assembly 150. For example, the one or more buttons 202 can be used to activate the pump system 150, pause the pump assembly 150, and clear system indicators such as one or more of the one or more indications 204. The one or more buttons 202 can by any type of switch or button, such as a touchpad, touch screen, keyboard, and so on. In some embodiments, the one or more buttons 202 can be a press button. In various implementations, one or more buttons 202 can be included on a touchscreen interface.

The pump assembly 150 can include a connector port 203 adapted to receive a connector 201. The connector 201 can be a part of the canister or the wound dressing that is attached to the pump assembly 150, as described above. The connector 201 can be removably attached to the connector port 203. In some arrangements, a first connector 201 can be removed from the pump assembly 150 and replaced with a second connector 201 that is then attached to the pump assembly 150. For example, a first connector 201 that is connected to a RENASYS™ dressing can be removed from the connector port 203 and replaced with a second connector 201 that connected to a PICO™ dressing, thereby allowing the pump assembly 150 to be switched from canister to a canisterless mode of operation. As described in more detail below, the connector 201 and/or pump assembly 150 can be adapted to allow the pump assembly 150 to detect whether a canister or canisterless connector 201 is attached to the connector port 203. In some arrangements, the operation of the pump assembly 150 can be adjusted according to whether the pump assembly 150 detects a canister or a canisterless connector 201 is connected to the connector port 203.

In some embodiments, the connector port 203 can include one or more connector switches in electrical communication with the control board 206, which can include one or more controllers. The one or more connector switches can be configured to engage one or more connectors of the canister or the dressing. In some embodiments, the one or more connector switches can advantageously permit the pump assembly 150 (e.g., the control board 206) to differentiate between a canister connection and a dressing connection. In some embodiments, one or more of the connectors 201 can include one or more connector switches in addition to or in lieu of the one or more connector switches of the connector port 203. The connector switches contemplated herein can be mechanical, electrical, optical, and/or magnetic, or any other suitable switch, and can include sensors and the like. The connector switches can be configured to close or open an electrical circuit, thereby permitting the control board 206 to detect whether the connector switch is engaged or disengaged. For example, as described in more detail below, the connector port 203 can include a connector switch that is actuated by a portion of a connector 201 that couples a canister to the connector port 203. The connector switch can be further configured so that the switch is not actuated by a connector 201 that couples a dressing to the connector port 203, thereby allowing the control board 206 to detect whether a canister or a dressing is attached to the connector port 203. In some arrangements, the pump assembly 150 can be configured so that the connector switch is activated by a connector 201 that couples a dressing to the connector port 203 and is not activated by a connector 201 that couples a canister to the connector port 203.

With continued reference to FIG. 3A, the one or more indicators 204 can indicate one or more operating or failure conditions of the pump assembly 150. Each of the one or more indicators 204 may provide an indication regarding a different operating or failure condition. In some implementations, an active (e.g., lit) indicator of the one or more indicators 204 can represent a certain operation condition for the pump assembly 150. For example, a dressing indicator of the one or more indicators 204 can provide an indication as to presence of leaks in the TNP system 100, and an active dressing indicator can represent a leak. As another example, a dressing capacity indicator of the one or more indicators 204 can provide an indication as to the remaining fluid capacity of the wound dressing or canister, and an active dressing capacity indicator can represent that the wound dressing or canister is at or nearing capacity. As yet another example, a battery indicator of the one or more indicators 204 can provide an indication as to remaining capacity or life of a power source, such as batteries, and an active battery indicator can represent a low capacity. In some embodiments, the one or more indicators 204 can represent a combination of one or more of the above operating or failure conditions of the pump assembly 150 or other operating or failure conditions for the pump assembly 150.

In some implementations, the one or more indicators 204 can be icons. For example, the one or more indicators 204 can be activated (e.g., lit) via an illumination source such as LEDs (not shown) of pump assembly 150. The one or more indicators 204 can, for instance, be of a different color, two different colors (e.g., two indicators can share the same color), or same color. In some embodiments, the pump assembly 150 can include visual, audible, tactile, and other types of indicators or alarms configured to signal to the user various operating conditions. Such conditions include system on/off, standby, pause, normal operation, dressing problem, leak, error, and the like. The indicators can include speakers, displays, light sources, etc., or combinations thereof. In various implementations, one or more buttons indicators 204 can be included on a touchscreen interface.

The pump assembly 150 can be powered by a power source 208 such as a battery power cell or any other suitable power source. The pump assembly 150 can also include a source of negative pressure 210, which can include a pump 212 powered by an actuator 214, such as an electric motor. In some embodiments, the actuator 214 is integrated into the pump 212. The negative pressure source 210 can be a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, a pump operated by a voice coil actuator, or any other suitable pump or micropump or any combinations of the foregoing. The pump assembly 150 can also include one or more pressure sensors 216 that measure pressure in the fluid flow path.

The pump assembly 150 can further include an inlet 218 to connect the pump assembly 150 to the wound dressing. For example, the inlet 218 can be connected to the connector port 203 and the connector 201 that is in fluid communication with the wound dressing via a fluid flow path.

The pump assembly 150 can also include an outlet 220. The outlet 220 can vent or exhaust gas to the atmosphere. In some embodiments, a filter (not shown) can be interposed between the outlet 220 and the atmosphere. The filter can provide filtration of the gas prior to venting the gas to the atmosphere. The filter can be a bacterial filter, odor filter, or any combination thereof. In some embodiments, a dampening component (not shown), such as a noise dampening component, can be interposed between the outlet 220 and the atmosphere. The dampening component can reduce the noise generated by the pump assembly 150 during operation. In some implementations, the pump assembly 150 can communicate information, such as information related to provision of negative pressure therapy, to one or more remote devices. Such communication can be performed using a wired or wireless interface.

Figure 3B:
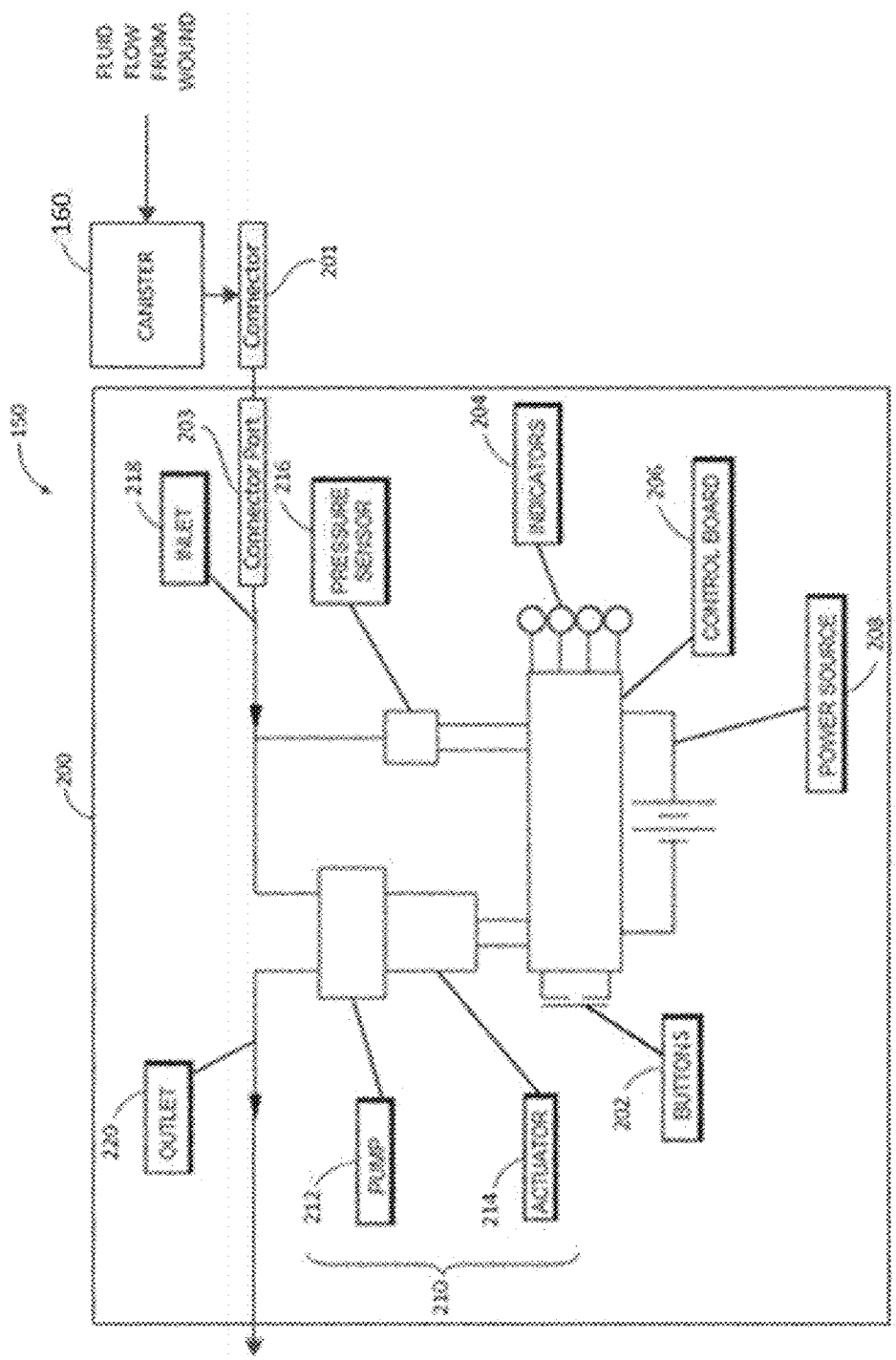

FIG. 3B illustrates the pump assembly 150 of FIG. 3A with a canister 160 additionally positioned in a fluid flow path between the inlet 218 and the wound dressing. In the illustrated embodiment, the connector 201 fluidically connects the canister 160 to the connector port 203. As discussed further below, the connector 201 can be configured to signal to the pump assembly 150 whether the connector port 203 is connected to a wound dressing directly or whether a canister 160 is disposed between the connector 203 and the wound dressing.

In some embodiments, the control board 206 (e.g., a controller) adjusts one or more operational parameters of negative pressure wound therapy depending on whether the pump assembly is connected to the canister or the dressing. For example, in canisterless mode, the level of negative pressure provided to the wound can be reduced compared to canister mode because the wound is exuding a smaller amount of fluid. As another example, detection of one or more operating conditions can be enabled, disabled, or adjusted. For instance, in canisterless mode, canister full detection (or blockage detection) and alarming can be disabled and, instead, dressing full detection and alarming can be enabled.

In some embodiments, the pump assembly 150 includes a user interface, such as one or more displays, indicators, lights, buttons, switches, speakers, vibrating elements, etc. The user interface can be adjusted based on detection of a canister. For example, in canister mode, the user interface can include an indicator alerting a user when canister becomes full. In canisterless mode, this indicator can be replaced with an indicator alerting the user when the dressing become full. In some embodiments, the indicators are icons.

Figure 4:
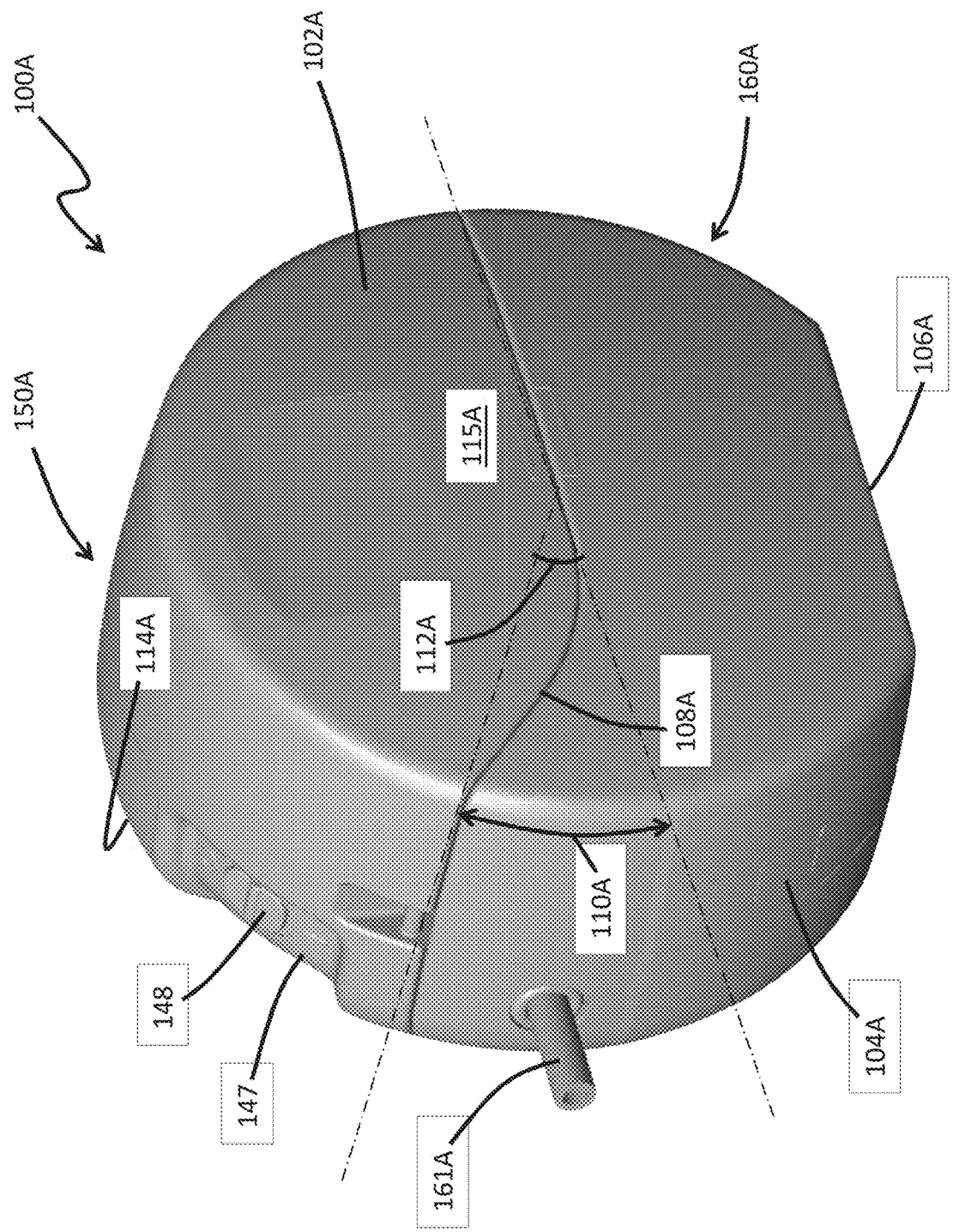
FIG. 4 is a front perspective view showing the front and right sides of an embodiment of the TNP system with a canister attached to the pump assembly.

FIG. 4 depicts in a perspective view an embodiment of the TNP system 100A with a canister 160A attached to the pump assembly 150A. The canister 160A can have an inlet 161A through which wound exudate can enter the canister 160A. As shown in FIG. 4, the TNP system 100 can have a disc-shaped or at least partially circular form when the pump assembly 150A is attached to the canister 160A and the system is viewed from the left or right side. For ease of discussion, each opposing surface or side of the TNP system 100A that has an at least partially circular shape will be referred to as a face 102A. The surface of the TNP system 100A that connects the two opposing faces 102A will be referred to as an edge 104A. In FIG. 4, the inlet 161A protrudes from the edge 104A of the canister 160A. For ease of discussion, the portion of the edge 104A from which the inlet 161A protrudes will be referred to as the front of the TNP system 100A. Accordingly, FIG. 4 shows a partial front and right view of the TNP system 100A. However, from the perspective of the TNP system 100A, the left face 115A of the TNP system is visible when the TNP system 100A is viewed from the right. The right face 114A of the TNP system 100A is not visible in FIG. 4. As shown in FIG. 4, the pump assembly 150A can include an on/off switch 148. In the illustrated embodiment, the on/off switch 148 is located in a recessed portion 147 of the edge 104A. Specifically, the on/off switch 148 is located on the front of the pump assembly 150A and toward the left face 114A of the pump assembly 150A.

With continued reference to FIG. 4, the edge 104A of the canister 160A can have a flat bottom surface or base 106A that extends between the front and rear of the canister 160A.

The base 106A may form a flat or linear surface. The base 106A can encourage orienting the TNP system 100 so that the on/off switch 148 is vertically above the inlet 161, as shown in FIG. 4. As discussed in more detail below, the TNP system 100 can be adapted to minimize or prohibit liquid (e.g., wound exudate) within the canister 160A from wetting components of the pump assembly 150A when the TNP system is supported on the base 106A.

The TNP system 100A can have a seam 108A at the interface between the pump assembly 150A and the canister 160A. According to the reference system set forth above to describe the TNP system 100A, the seam 108A is at the interface between a top surface of the canister 160A and a bottom surface of the pump assembly 150A. As shown in FIG. 4, a portion of the seam 108A can run substantially parallel to the base 106A. In the illustrated embodiment, the seam 108A rises toward the top of the TNP system 100A as the seam 108A approaches the inlet 161A in a direction from the rear of the TNP system 100A to the front of the TNP system 100A. The amount the seam 108A rises relative to the portion of the seam 108A that is parallel to the base 106A can be defined by an arc length 110A, as indicated in FIG. 4. A canister angle 112A can be defined that corresponds to the arc length 110A such that the arc length 110A is equal to the radius of the face 102A multiplied by the canister angle 112A, as shown in FIG. 4. In the illustrated embodiment, the canister angle 112A is about 30 degrees. In some embodiments, the canister angle 112A can be an angle of: 10 degrees, 20 degrees, 40 degrees, 60 degrees, or a value between any of these aforementioned values. As discussed in more detail below, the canister angle 112A can be selected to prevent or minimize liquid (e.g., wound exudate) within the canister 160A from wetting components of the pump assembly 150A.

FIGS. 5A-B illustrate another example of a TNP system 1100 that uses the same pump assembly 1150 when the TNP system 1100 operates in either canisterless mode (FIG. 5A) or canister mode (FIG. 5B). The pump assembly 1150 is shown schematically, and may comprise any of the pump assemblies described elsewhere in this specification. In some embodiments, different types of connectors may be utilized to connect to the pump assembly 1150, and the pump assembly 1150 may be configured to determine a desired mode of operation based on the type of connector used, as described in more detail below. Moreover, any of the features of the pump assemblies, adapters and connectors described hereinbelow may be utilized with any of the embodiments of the pump assemblies or other components described elsewhere in this specification.

FIG. 5A shows that a canisterless-mode dressing 1182 can be used to dress the wound when the pump assembly 1150 is connected to the wound dressing without a canister interposed along the flow path between the wound and the pump assembly 1150. In some embodiments the canisterless-mode dressing 1182 can be a dressing for covering and protecting a wound. The canisterless-mode dressing 1182 may be in fluid communication with the pump assembly via an attached fluid conduit, such as a flexible conduit 1172, described further below. The canisterless-mode dressing 1182 is shown schematically, and may comprise any of the canisterless-mode dressings described elsewhere in this specification, including, for example absorbent dressings such as PICO available from Smith & Nephew. Moreover, any of the canisterless-mode dressings, conduits and flexible connectors described hereinbelow may be utilized with any of the embodiments of the pump assemblies or other components described elsewhere in this specification.

In some embodiments, a suitable canisterless-mode dressing comprises a backing layer and one or more absorbent layers beneath the backing layer. A wound contact layer may be provided beneath the one or more absorbent layers. A moisture vapor permeable backing layer may be utilized that permits evaporation of wound exudate through the backing layer. In some embodiments, one or more absorbent layers of the wound dressing may be placed in direct contact with the backing layer to facilitate evaporation. In other embodiments, one or more transmission layers may be located between the backing layer and the absorbent layer(s), and or between the absorbent layer(s) and the wound contact layer. These transmission layers may be made of foam, 3D fabric or other suitable materials.

In some embodiments, a liquid barrier may be utilized to prevent wound exudate from passing from the canisterless wound dressing either to or beyond the connector 1172. For example, a liquid barrier can be located underneath the backing layer, between the backing layer and the flexible connector, or may be located within the flexible connector. Liquid barriers may be constructed of hydrophobic or hydrophilic materials, including for example a hydrophobic membrane like microporous ePTFE. Further examples of canisterless-mode dressing constructions and liquid barriers that may be utilized are described in U.S. Pat. No. 7,779,625 filed on Dec. 13, 2006, and in U.S. Pat. No. 8,764,732 filed on Sep. 20, 2010, and in U.S. Pat. No. 9,061,095 filed Apr. 21, 2011, and in PCT Publication No. WO 2013/175306, filed May 22, 2013, and in U.S. Patent Application Publication No. 2016/0339158 filed May 18, 2015, and in U.S. Patent Application Publication No. 2015/0216733, filed Jan. 30, 2015, each of which applications is incorporated by reference herein.

In some embodiments, the wound dressing 1182 may be an Avelle wound dressing being promoted by ConvaTec, such as described in PCT Publication No. WO 2017/196888, the entirety of which is hereby incorporated by reference. The canisterless-mode dressing 1182 can include an adhesive layer for adhering the dressing adjacent the wound, a wound contact layer, a pressure dispersion layer, a plurality of layers of absorbent material disposed between the wound contact layer and the pressure dispersion layer, a backing layer having a first surface and a second surface, the first surface of the backing layer being adjacent, and in contact with, the pressure dispersion layer and the adhesive layer. A flexible connector 1172 can be disposed on the second surface of the backing layer.

In some embodiments, the canisterless dressing comprises: a wound contact layer, the wound contact layer having a first surface and a second surface, the wound contact layer further having a peripheral region and a central region, wherein the first surface of the wound contact layer contacts the wound when the dressing is adhered to skin adjacent the wound, a pressure dispersion layer having a peripheral region and a central region, a plurality of layers of absorbent material disposed between the second surface of the wound contact layer and the pressure dispersion layer, and, an envelope formed by joining the peripheral region of the pressure dispersion layer with the peripheral region of the second surface of the wound contact layer, the plurality of layers of absorbent material being disposed substantially within an interior cavity of the envelope. Alternately, an envelope may be formed by joining the peripheral region of a thermoplastic spun lace layer connected to the pressure dispersion layer with the peripheral region of a nonwoven spun lace layer connected to the second surface of the wound contact layer, such that the plurality of layers of absorbent material are disposed substantially within an interior cavity of the envelope. In some embodiments, the dressing can comprise a thermoplastic spun lace layer connected to the pressure dispersion layer, and a nonwoven spun lace layer connected to the wound contact layer, and wherein the envelope is formed by joining peripheral portions of the thermoplastic spun lace layer and the nonwoven spun lace layer, wherein the interior cavity of the envelope is formed by the nonwoven spun lace layer and the thermoplastic spun lace layer, and wherein the plurality of layers of absorbent material are disposed substantially within an interior cavity of the envelope.

In one embodiment, the connector 1172 can be a flexible conduit comprising an elongate upper film layer, an elongate lower film layer, and an elongate spacer material positioned between the upper and lower film layers. The upper and lower film layers can be formed from polyvinyl chloride, polyurethane, or any other suitable material. The elongate spacer material may be made of a material resistant to collapsing in at least one direction thereby enabling effective transmission of negative pressure therethrough. One embodiment of an elongate spacer material comprises three dimensional fabric material. Other embodiments of the spacer material may include various materials including, but not limited to, nylon. The spacer material can comprise a lattice structure. In at least one embodiment, the spacer material can comprise a tube knitted or braided from a monofilament yarn. The use of a knitted or braided monofilament to form a tube is advantageous as the resulting tube is flexible and resilient. The monofilament yarn can also act as a filter, preventing or reducing the extent to which relatively large pieces of material that might cause an obstruction in the conduit connecting the dressing to the pump assembly can be drawn from the wound dressing into the conduit. The monofilament yarn can be of any material conventionally used to produce such yarns, for example, polyester, polyamide, polyethylene, polypropylene, and polybutylene terephthalate. The shape, material, and arrangement of the spacer material can be adapted to enable continued fluid flow along the flexible connector 1172 while a negative pressure generated by the pump assembly 1150 is transmitted to the wound through the flexible connector 1172.

The upper film layer, lower film layer and/or the elongate spacer material may be rectangular in shape, or in some embodiments, may have an enlarged distal end, such as shown in FIG. 53A with an enlarged circular or teardrop shape distal end, configured to be positioned over an opening in the backing layer of the wound dressing. The distal end of the lower film layer may have one or more openings positioned over the opening in the backing layer of the wound dressing to communicate negative pressure to the wound dressing.

In some embodiments, a filter element may be provided to cover the opening in the backing layer and partially or entirely prevent the passage of wound exudate into the flexible conduit. The filter element may be positioned beneath the backing layer, above the backing layer and beneath the flexible conduit, or above the lower film layer of the flexible conduit. In at least one embodiment, the filter element is disposed between the backing layer and the elongate lower film layer of the flexible connector 1172. The filter element can be adapted to allow gas to pass through the filter element while preventing or inhibiting liquid from passing through the filter element. The filter element may comprise a hydrophobic membrane. In some embodiments, the filter element may comprise a hydrophilic material. The filter element may comprise hygroscopic fibers that become moist, slippery, or gelatinous upon the wetting of the fibers. In some embodiments, the filter element comprises sodium carboxymethylcellulose fibers, chemically modified cellulosic fibers, alkyl sulphonate modified cellulosic fibers, pectin fibers, alginate fibers, chitosan fibers, hyaluronic acid fibers, other polysaccharide fibers, or fibers derived from gums.

The proximal end of the flexible conduit may comprise a port or connector configured to connect the flexible conduit directly or indirectly to a source of negative pressure (e.g., a pump assembly 1150). In some embodiments, a valve, such as a check valve, a one-way valve or non-return valve, may be provided at the proximal end of the flexible conduit, for example in the port or connector. The one-way valve can allow fluid to flow towards the pump assembly 1150 while preventing fluid flow away from the pump assembly 1150 and towards the dressing. Suitable valves may include silicone valves and duck bill style valves. The valve may be utilized to maintain negative pressure under the wound dressing should the flexible conduit be disconnected from the source of negative pressure. Further details regarding embodiments of flexible conduits, spacer materials, filter elements, and valves that may be utilized with canisterless dressings are described in PCT Publication No. WO 2013/175306, and in PCT Publication No. WO 2016/184916, each of which publications is hereby incorporated by reference in its entirety.

As shown in FIG. 5A, the canisterless-mode wound dressing 1182 can include a distal conduit 1170 that extends from the wound dressing 1182 and flexible connector 1172 to a conduit adapter 1190. The TNP system 1100 can include a proximal conduit 1200 that extends from the conduit adapter 1190 to the pump assembly 1150. The proximal conduit 1200 can be connected to the pump assembly 1150, such as to an inlet, by a pump connector 1300. As shown in FIG. 5A, the proximal conduit 1200 can be a dual lumen conduit that has first tubing 1202 and a second tubing 1204. The first tubing 1202 and the second tubing 1204 can be fluidically isolated from one another throughout the portion of the proximal conduit 1200 that extends between the pump assembly 1150 and the conduit adapter 1190. The conduit adapter 1190 can include a button 1192 that allows the proximal conduit 1200 to be disconnected from the distal conduit 1170.

In some embodiments, the proximal conduit 1200 is a dual lumen conduit configured to provide another fluid flow path to the wound dressing that is separate from the fluid flow path configured to aspirate fluid from the wound. For example, one of the branches of the dual lumen conduit, such as first tubing 1202 (or second tubing 1204) can function as a fluid flow path configured to aspirate fluid from the wound, while the other of the branches of the dual lumen conduit, such as the second tubing 1204 (or the first tubing 1202) is configured to provide another fluid flow path. Another lumen can be terminated at the wound dressing or another location, such as the adapter 1190. Utilizing the dual lumen conduit can provide one or more of the following advantages: monitoring pressure at the wound, allowing atmospheric air or another gas or fluid to enter the fluid flow path configured to aspirate fluid from the wound in order to clear a blockage in the fluid flow path, determining presence of one or more operating conditions, such as a blockage, leak, or the like in the fluid flow path.

In some embodiments, a first branch of the dual lumen conduit of a TNP system can be fluidically connected to a first location in the fluid flow path and the second branch of the dual lumen conduit can be fluidically connected to a second location on the fluid flow path that is different from the first location. Such arrangement can permit measuring pressures in different locations in the fluid flow path and determining a difference between the measured pressures by using separate pressure sensors or a differential pressure sensor. Based at least on the determined difference, one or more operating conditions can be determined. For example, the first location can be proximal the wound and the second location can be downstream of the first location, such as downstream of the canister. Blockage at or near the wound can be detected by determining that pressure at the first location is at least a first threshold amount lower (or more positive) than pressure at the second location. In some implementations, the TNP system can attempt to clear the blockage by introducing gas, such as atmospheric air, into the first branch of the dual lumen conduit. This can be accomplished by opening a valve that is in fluidic communication with the first branch.

As another example, a leak at or near the wound can be detected by determining that pressure at the first location is at least a second threshold amount lower (or more positive) than pressure at the second location and remains at least the threshold amount lower when the negative pressure source is operated to increase (or make more negative) the amount of negative pressure provided to the wound. Detection and/or addressing the one or more operating conditions described in the preceding paragraphs as well as elsewhere in the specification can be performed by or under control of a controller of the TNP system. Additional details of detection and addressing the one or more operating conditions are described in U.S. Pat. No. 8,617,129, filed Nov. 11, 2008, which is incorporated by reference in its entirety.

FIG. 5B illustrates the TNP system 1100 when the system 1100 is operating with a canister 1160 disposed along the flow path between the pump assembly 1150 and a canister-mode wound dressing 1181. The canister-mode dressing 1181 and canister 1160 are shown schematically, and may comprise any of the canisters-mode dressings and canisters described elsewhere in this specification, including, for example foam or gauze, backing layers or drapes, and canisters available with RENASYS dressings from Smith & Nephew. Moreover, any of the canister-mode dressings, conduits and connectors, and canisters described hereinbelow may be utilized with any of the embodiments of the pump assemblies or other components described elsewhere in this specification.

As shown in FIG. 5B, the pump assembly 1150 can be configured to couple to the canister 1160 via a connection 1162. For example, the pump assembly 1150 can seat onto a bulkhead 1162 of the canister 1160 such that the pump assembly 1150 is docked with the canister 1160. The interior space or reservoir of the canister 1160 can contain a canister filler material. The canister filler material can be a material that swells and forms a semisolid material when wound exudate is drawn into the canister reservoir and mixes with the canister filler material.

As discussed in more detail below, the TNP system 1100 can be configured so that a flow path through the pump assembly 1150 is modified depending on whether the pump assembly 1150 is seated onto the bulkhead 1162. For example, the pump assembly 1150 can move fluid along a first flow path 11 (shown in FIG. 5B) when the pump assembly 1150 is seated on the bulkhead 1162 and can move fluid along a second flow path 22 (shown in FIG. 5A) when the pump assembly 1150 is unseated from the bulkhead 1162, the first flow path 11 being different from the second flow path 22.

The canister-mode dressing 1181 can be different from the canisterless-mode dressing 1182. The canister-mode dressing 1181 can include a flexible bridge 1173 that connects the pump assembly 1150 to a drape positioned over a wound. Pressure distribution material, such as one or more pieces or layers of open cell foam, may be positioned beneath the drape. The flexible bridge 1173 can be similar to the flexible connector 1172 or may have a different structure as described below. The lumen of the flexible bridge 1173 can be enlarged compared to the flexible connector 1172 to accommodate a larger flow of wound exudate. Whereas the flexible connector 1172 is not adapted in some embodiments to transport wound exudate, the flexible bridge 1173 may comprise a spacer material configured to transport wound exudate to the canister 1160. The flexible bridge 1173 can comprise an open-cell foam material. The flexible bridge 1173 can be adapted to maintain a flow pathway through the distal conduit 1170 when the pump assembly 1150 applies a negative pressure to the canister-mode wound dressing 1181.

In some embodiments, the flexible connector 1172 or the flexible bridge 1173 may utilize an alternative material configured to extend between the wound dressing and the distal conduit 1170. For example, a three dimensional fabric material may be utilized. Other materials that may be utilized are described in PCT Publication No. WO 2013/175306, filed May 22, 2013, and in U.S. Patent Application Publication No. 2016/0339158 filed May 18, 2015, and in U.S. Patent Application Publication No. 2010/0324516 filed Jun. 18, 2009, and in U.S. Pat. No. 8,162,907, filed Jan. 20, 2009, each of which applications is incorporated by reference herein. In some embodiments, a non-return valve may be located at the proximal end of the flexible connector 1172 or the flexible bridge 1173, to allow disengagement of the wound dressing and flexible connector 1172 or the flexible bridge 1173 from the pump assembly 1150 while maintaining negative pressure. In other embodiments, a non-return valve may be placed in other locations, such as at the conduit adapter 1190. The flexible connector 1172 or the flexible bridge 1173 may be pre-attached to a wound cover 120 utilized to cover the wound, or may be provided as a separate component. The flexible connector 1172 or the flexible bridge 1173 and the material inside the flexible connector 1172 or the flexible bridge 1173 may have an enlarged distal end to be located over the wound filler 130, such as a teardrop shape or rounded end.

Figure 6:
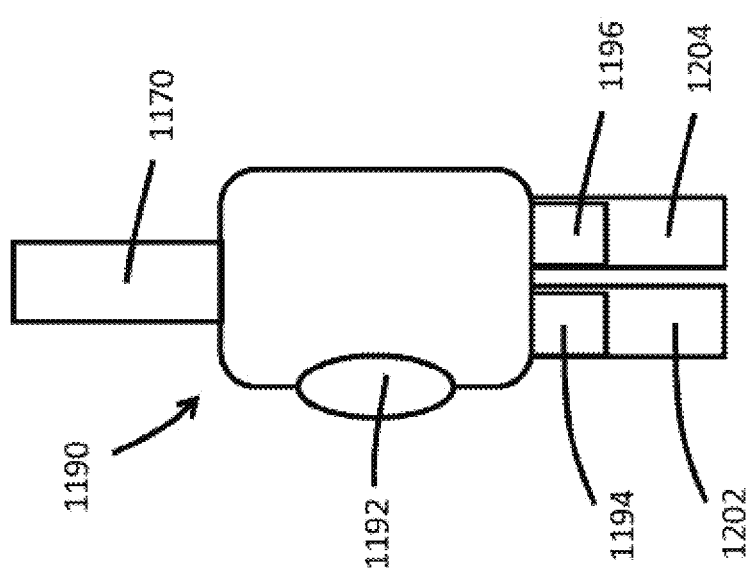
FIG. 6 illustrates a conduit adapter that can connect a distal conduit with a proximal conduit.

FIG. 6 shows an embodiment of the conduit adapter 1190. As shown in FIG. 6, the conduit adapter 1190 can have a first port 1194 that connects with the first tubing 1202 of the proximal conduit 1200. The conduit adapter 1190 can have a second port 1196 that connects with the second tubing 1204 of the proximal conduit 1200. In some arrangements, the first and second tubing 1202, 1204 can be formed as one member with two lumens. In some embodiments, the first tubing 1202 is configured to provide a flow path between the distal conduit 1170 and the pump assembly 1150. The conduit adapter 1190 can be color coded to indicate whether the conduit adapter 1190 is for use with a canister-mode dressing 1181 or a canisterless-mode dressing 1182. For example, the button 1192 and the first and second ports 1194, 1196 of the conduit adapter 1190A can be colored yellow to indicate that the conduit adapter 1190 is for use with a canisterless-mode dressing 1182. When the conduit adapter 1190 is for use with a canister-mode dressing 1181, the button 1192 and the first and second ports 1194, 1196 can be a color other than yellow (e.g., blue).

Figure 7:
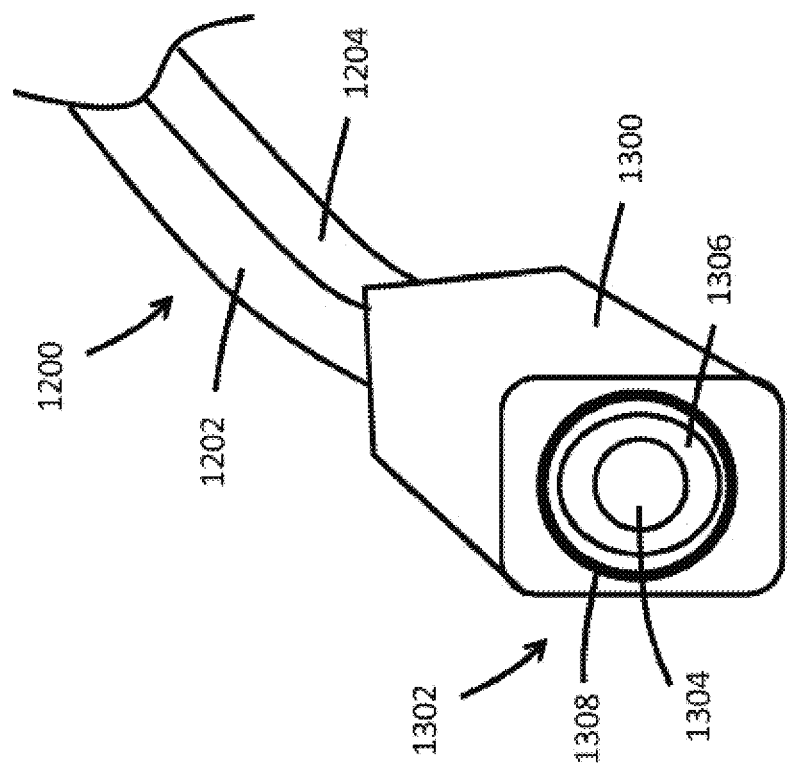
FIG. 7 illustrates a pump connector that can connect a proximal conduit to a pump assembly.

FIG. 7 shows a pump-side view of the pump connector 1300 that connects the proximal conduit 1200 to the pump assembly 1150. The pump connector 1300 has a pump interface 1302 that is adapted to form a fluid-tight seal with the pump assembly 1150. In the illustrated embodiment, the pump interface 1302 comprises an inner channel 1304 that is surrounded by a concentric annulus 1306. In some embodiments, the inner channel 1304 is in fluid communication with one of the tubes of the dual-lumen proximal conduit 1200 and the concentric annulus 1306 is in fluid communication with the other tube of the dual-lumen proximal conduit 1200. The pump interface 1302 can include a seal 1308 (e.g., O-ring) adapted to form a fluid-tight seal when the pump connector 1300 is inserted into the pump assembly 1150. The pump connector 1300 may also be provided with a portion that is colored (e.g., yellow) to indicate that the connector 1300 is to be used with a canisterless-mode dressing 1182A. The colored portion of the pump connector 1300 may be colored a color that is different from yellow (e.g., blue) to indicate that the connector 1300 is to be used with a canister-mode dressing 1181A.

Figure 8:
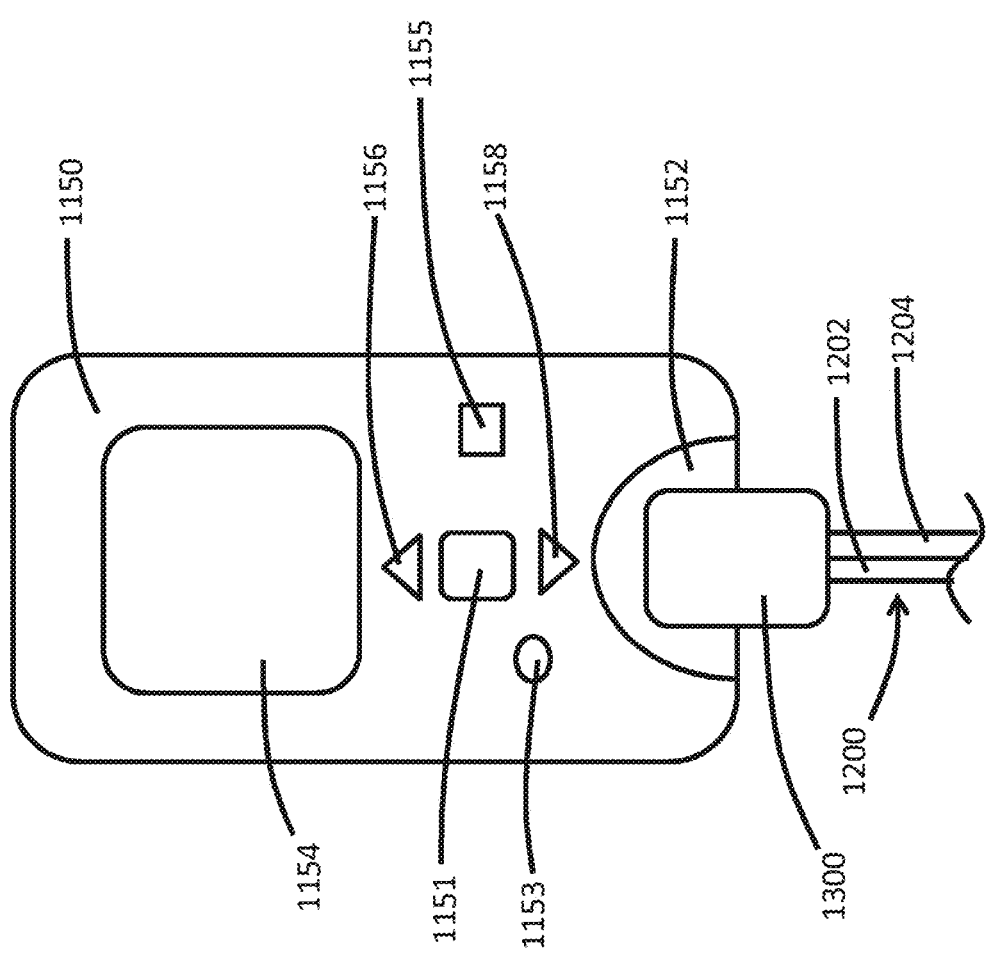
FIG. 8 illustrates a front view of a pump assembly operating in canisterless mode.

FIG. 8 shows the pump connector 1300 can be inserted into the pump assembly 1150 to establish a fluid flow connection between the pump assembly 1150 and the proximal conduit 1200. The pump assembly 1150 can include a visual indicator ring 1152. The visual indicator ring 1152 can surround an opening in the housing of the pump assembly 1150 through which the pump connector 1300 is inserted to connect the pump connector 1300 to the pump assembly 1150. The visual indicator ring 1152 can change color to inform a user of the status of the TNP system 1100. For example, the visual indicator ring 1152 can illuminate red to indicate the TNP system 1100 has not reached a threshold negative pressure set point. The visual indicator ring 1152 can illuminate green to indicate the TNP system 1100 has reached a threshold negative pressure set point at the wound. As another example, the visual indicator ring 1152 can illuminate red to alert or alarm one or more operating conditions of the TNP system 1100, such as blockage in the fluid flow path, disconnected canister, leak, overpressure, power source status, inactivity, or the like. In some embodiments, the visual indicator ring 1152 can provide a plurality of indications (such as, illuminate with plurality of colors) to allow a user to distinguish between the one or more errors. In some variants, the mode of illumination (such as steady illumination, quick flashing, slow pulsing) of the visual indicator ring 1152 can allow a user to distinguish between the one or more errors. The visual indicator ring 1152 can include a light guide (not shown) that projects light from one or more light sources, such as LEDs.

With continued reference to FIG. 8, the pump assembly 1150 can include a display 1154. The display 1154 can be an LED display. The display 1154 can display text and/or graphics to communicate information to a user. For example, the display can illustrate an animated bar pattern (or another animated or static pattern) when a pump is operating to provide negative pressure. The pump assembly 1150 can include one or more buttons that allow a user to interact with the pump assembly 1150. The pump assembly 1150 can have an up button 1156 and a down button 1158. The up and down buttons 1156, 1158 can allow a user to toggle through a menu that can be displayed on the display 1154. The pump assembly 1150 can include a select button 1151 that allows a user to make a selection within a menu. The pump assembly 1150 can include a selection indicator 1153. The selection indicator 1153 can be a light source, such as an LED, that flashes to indicate when a selection can be made. The pump assembly 1150 can include a back button 1155 which is used to move back to the previous menu. Browsing the menu and making selections can allow the user to adjust operation of the TNP system 1100, including adjusting the operational mode (for example, switching between canister and canisterless modes), changing the negative pressure set point, clearing the alarms, or the like. In some embodiments, the display 1154, the one or more buttons, and/or the visual indicator ring 1152 can make up a user interface. In some embodiments, switching between canister and canisterless mode can include presenting a new list of menu selections, alarms, threshold set points, and/or control algorithms. For example, the pump assembly 1150 can use one set of menu selections, threshold set points, and control algorithms when the pump assembly is operating in the canister mode and a different set of menu selections, threshold set points, and control algorithms when the pump assembly is operating in the canisterless mode.

The pump assembly 1150 can include one or more controllers, such as microprocessors. The one or more microprocessors can receive an input signal from the buttons (e.g., the up button 1156). The one or more microprocessors can send an output to the indicator ring 1152 or the display 1154. The one or more microprocessors can send an output to control a pump of the pump assembly 1150. The pump assembly 1150 can include a power source, such as one or more batteries. The pump assembly 1150 can operate in a mode in which the pump assembly 1150 is powered solely by the one or more batteries. The pump assembly 1150 can include one or more lumens that fluidically connect the inlet to one or more pressure sensors that measure pressure in the fluid flow path. The one or more microprocessor can control the pump based at least in part on the measured pressure and/or the negative pressure set point. The pump assembly 1150 can have a pump that is configured to provide a negative pressure to the wound dressing.

In some embodiments, the system 1100 may be modified to incorporate different mechanisms for detecting whether the pump assembly 1150 will be utilized with a canister or with a canister-less dressing. The system 1100 can have one or more switches that are activated differently depending on whether a canister-mode dressing 1181 or a canisterless-mode dressing 1182 is connected to the pump assembly 1150. In some arrangements, the one or more switches is activated by one but not the other of the canister-mode dressing 1181 or the canisterless-mode dressing 1182. Further details of switches that can inform the pump assembly 1150 whether a canister-mode dressing 1181 or a canister-less-mode dressing 1182 is attached to the pump assembly 1150 are described elsewhere in this specification and in U.S. Patent Application No. 62/459,537, filed Feb. 15, 2017, and in U.S. Provisional Application No. 62/459,511, filed Feb. 15, 2017, and entitled "NEGATIVE PRESSURE WOUND THERAPY APPARATUSES AND METHODS FOR USING THE SAME," and in U.S. Provisional Application No. 62/584,053, filed Nov. 9, 2017, and entitled "NEGATIVE PRESSURE WOUND THERAPY APPARATUSES AND METHODS FOR USING THE SAME," the entirety of each of which is applications incorporated by reference herein.

Figure 9:
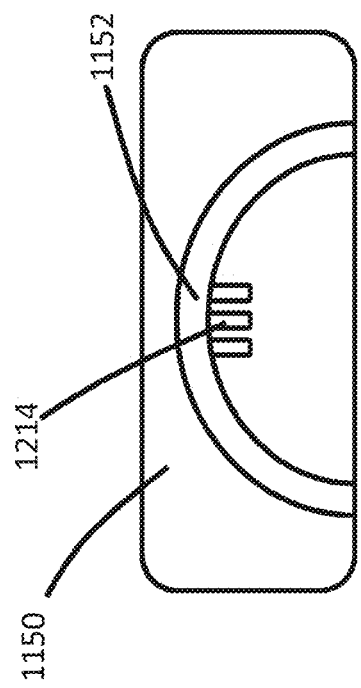
FIG. 9 illustrates an end view of a portion of the pump assembly that receives the pump connector.

FIG. 9 is an end view of the pump assembly 1150, looking into the portion of the pump assembly 1150 that receives the pump connector 1300. As shown in FIG. 9, the pump assembly 1150 can include one or more switches 1214 that are activated when the pump connector 1300 is inserted into or otherwise connected to the pump assembly 1150. In some embodiments, the one or more switches 1214 allow the pump assembly 1150 (such as, the one or more controllers) to detect the identity of the pump connector 1300 that is connected to the pump assembly 1150. For example, a first pump connector 1300 that is used with a first type of wound dressing may activate the switches 1214 differently compared with a second type of pump connector 1300 that is used with a second type of wound dressing. In some embodiments, activation of the switches 1214 enables the pump assembly 1150 to distinguish between a canister-mode pump connector and a canisterless-mode pump connector being attached to the pump assembly 1150. The switches 1214 can be configured to start a timer of the pump assembly 1150 (e.g., a lifetime timer that upon expiration causes the pump assembly 1150 to cease operation as described herein). The switches 1214 can detect a type of pump connector electrically (such as based on resistance, capacitance, or the like), magnetically, or the like using wired or wireless interface. In some cases, proximity detection, optical detection, RFID detection, bar code detection, or another wireless interface can be used.

FIG. 10 shows a backside view of the pump assembly 1150 when the pump assembly 1150 is operating in canisterless mode. The pump assembly 1150 can have a canister interface 1400 on the backside of the pump assembly 1150. The canister interface 1400 can have one or more pump connection ports 1402 that align with corresponding canister ports 1164 (shown in FIG. 11) disposed on the canister bulkhead 1162 to establish a flow path between the pump assembly 1150 and the canister 1160. The pump connection ports 1402 can be disposed on a contoured surface portion 1401 of the pump interface 1400. The contoured surface portion 1401 can be raised or recessed relative to an adjacent surface portion 1403 of the canister interface 1400. The canister interface 1400 can include a seating switch 1404 that is actuated when the pump assembly 1150 is seated onto the canister 1160. Actuation of the seating switch 1404 can change the flow path of fluid through the pump assembly 1150 from a first flow path 11 to a second flow path 22 (shown in FIGS. 5A and 5B).

Figure 11:
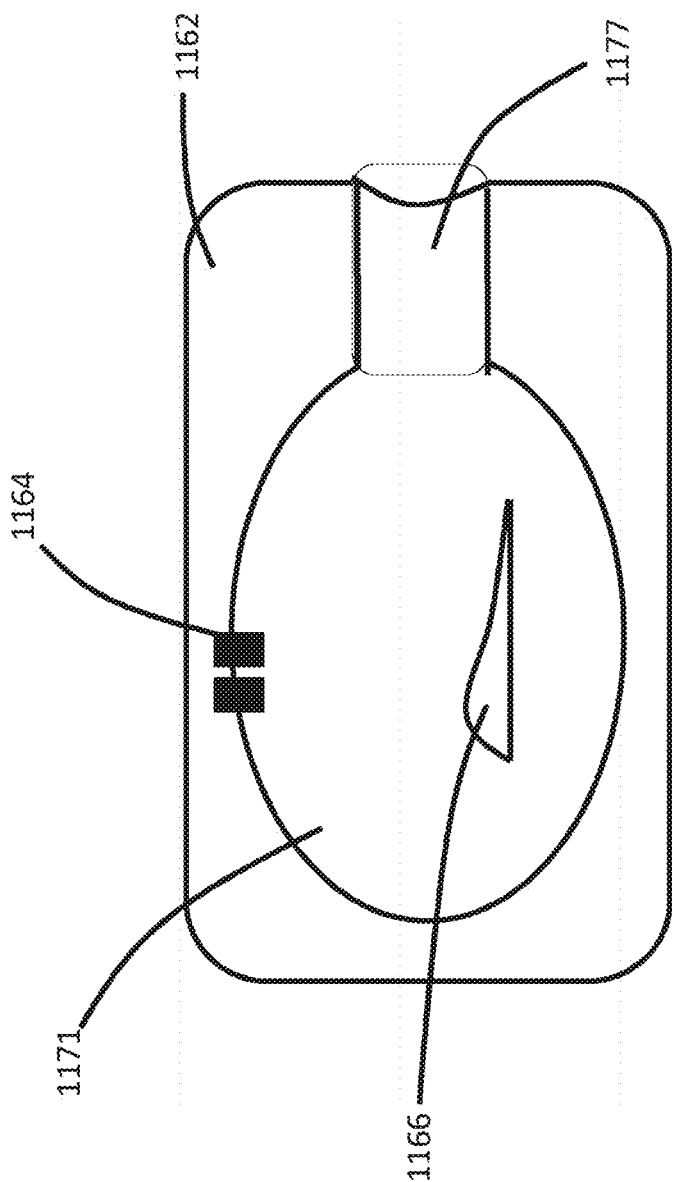
FIG. 11 illustrates a top view of a canister bulkhead that receives the pump assembly when the TNP system is operating in canister mode.

FIG. 11 shows a top view of the canister bulkhead 1162. The canister bulkhead 1162 can seal a top mouth of the canister 1160 that is used when the pump assembly 1150 is connected to a canisterless-mode dressing 1181. FIG. 11 shows the surface of the canister bulkhead 1162 that faces away from the interior space of the canister 1160 when the bulkhead 1162 is seated onto the mouth of the canister 1160. The canister bulkhead 1162 can have a bed 1171 sized to receive the pump assembly 1150 when the pump assembly 1150 is seated onto the canister bulkhead 1162. The canister bulkhead 1162 can include a trough 1177 that extends from the bed 1171 to an edge of the canister bulkhead 1162, as shown in FIG. 11. The trough 1177 can be sized to receive at least a portion of the pump connector 1300 or proximal conduit 1200 that extend from pump assembly 1150. The canister bulkhead 1162 can include one or more canister connection ports 1164 that align with corresponding pump connection ports 1402A (shown in FIG. 10) disposed on the pump assembly 1150. As shown in FIG. 11, the one or more canister connection ports 1164 can be disposed on the bed 1171 of the bulkhead 1162. The canister bulkhead 1162 can include an arm 1166 that is configured to activate the seating switch 1404 of the pump assembly 1150 when the pump assembly 1150 is seated onto the canister bulkhead 1162. Activation of the seating switch can change the flow path through the pump connection ports 1402 so that the pump assembly 1150 applies suction to the canister 1160 through the canister connection ports 1164.

In some arrangements, connection of the pump assembly 1150 to a canister bulkhead 1162 can preclude the pump assembly 1150 from being connected to a canisterless-mode dressing 1182. For example, the pump connector 1300 associated with a canisterless-mode dressing 1182 may be differently sized compared to a pump connector 1300 associated with a canister-mode dressing 1181. The TNP system 1100 can be configured so that seating the pump assembly 1150 onto the canister bulkhead 1162 can modify or obscure the portion of the pump assembly 1150 that receives the pump connector 1300 such that a canisterless-mode dressing 1182 cannot be attached to the pump assembly 1150 when the pump assembly 1150 is seated on the canister bulkhead 1162. In certain arrangements, connection of a canisterless-mode dressing 1182 to the pump assembly 1150 can preclude the pump assembly 1150 from being seated onto the canister bulkhead 1162.

Figure 12:
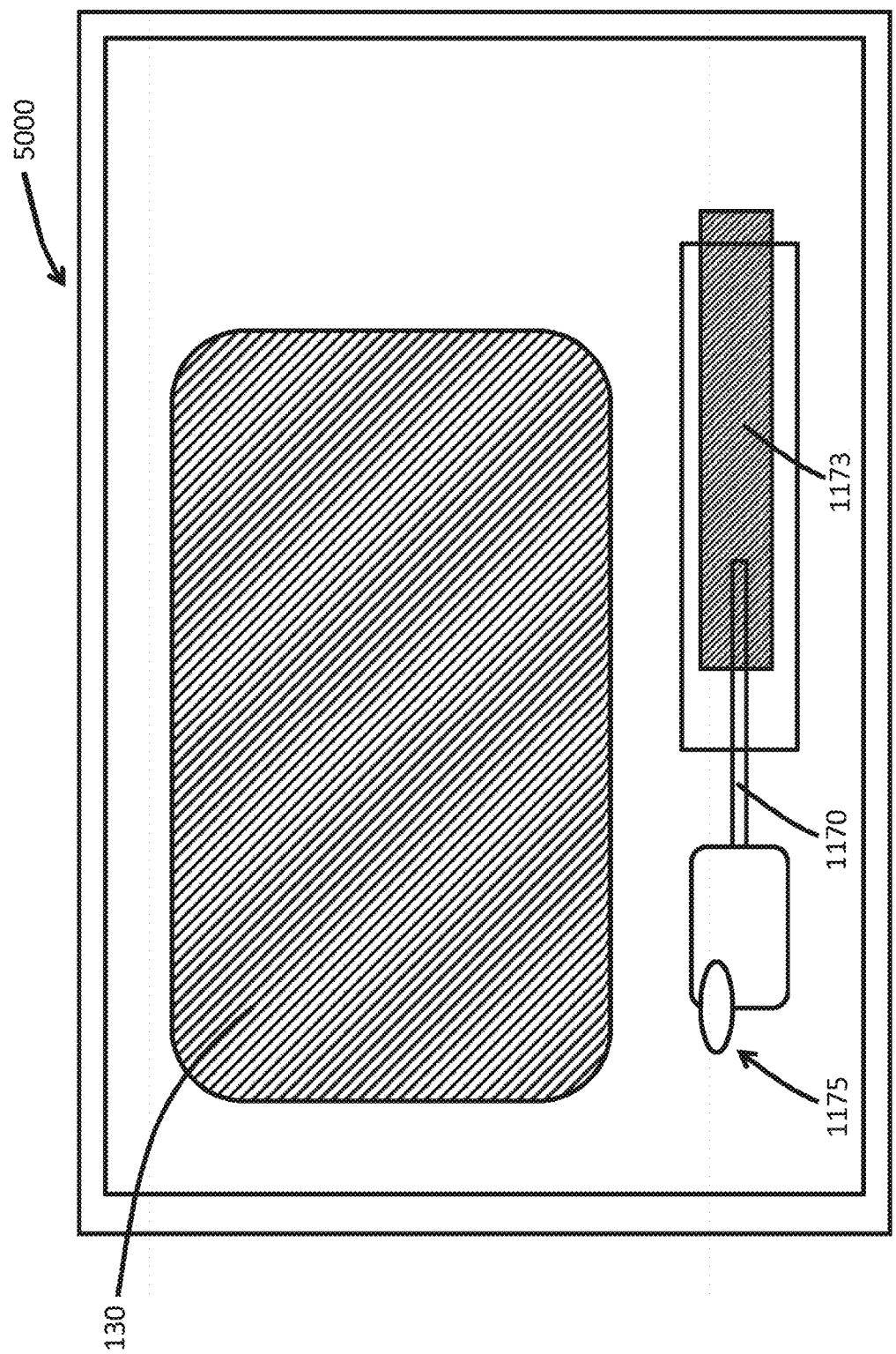
FIG. 12 illustrates a packaging of components of a canister-mode dressing according to some embodiments.

FIG. 12 shows a packaging element 5000 (such as a box, a tray or other element) that can be used to package the components of a canister-mode dressing 1181. Two or more components of the canister-mode dressing 1181 can be packaged together. For example, the flexible bridge 1173, wound filler such as the pressure distribution material described above, and/or other components (e.g. drapes or backing layers, adhesive elements, the conduit adapter 1190 and the pump connector 1300) of the canister-mode dressing 1181 can be packaged together. The flexible bridge 1173 can be attached to a connection feature 1175 that is used to fluidically connect the flexible bridge 1173 with the conduit adapter 1190 or another component of the system (such as directly to the pump assembly). The connection feature 1175 can be color coded, for example to indicate which conduit adapter 1190 is to be used with the connection feature 1175 or which mode the dressing 1181 is to be used with. For example, the connection feature 1175 of the canister-mode dressing 1181 and the conduit adapter 1190 can both be colored blue to indicate that the conduit adapter 1190 is intended for use with a canister-mode dressing 1181.

In some embodiments, the TNP system 1100 can be packaged as a negative pressure wound therapy kit. The kit can include one or more components selected from the group consisting of: a pump assembly 1150, a wound dressing (e.g., a canisterless-mode dressing 1182, a canister-mode dressing 1181), a flexible connector 1172, a flexible bridge 1173, a distal conduit 1170, a proximal conduit 1200, a pump connector 1300, a conduit adapter 1190, wound filler 130, a wound contact layer, an absorbent layer, a backing layer, and a canister 1160. One or more components of the negative pressure wound therapy kit can be packaged separately from the pump assembly 1150. In certain arrangements, one or more components of the negative pressure wound therapy kit are packaged together with the pump assembly 1150. In some embodiments, the wound dressing for either canister mode or canisterless mode is packaged together with some or all of the conduits and adapters that are used to connect the wound dressing to the pump assembly. In some embodiments, the kit includes two or more dressings. For example, the kit can include components for a canister-mode dressing 1181 and components for a canisterless-mode dressing 1182. Other embodiments of the kit may comprise two dressings of the same type (e.g., two or more canisterless-mode dressings).

Figure 13:
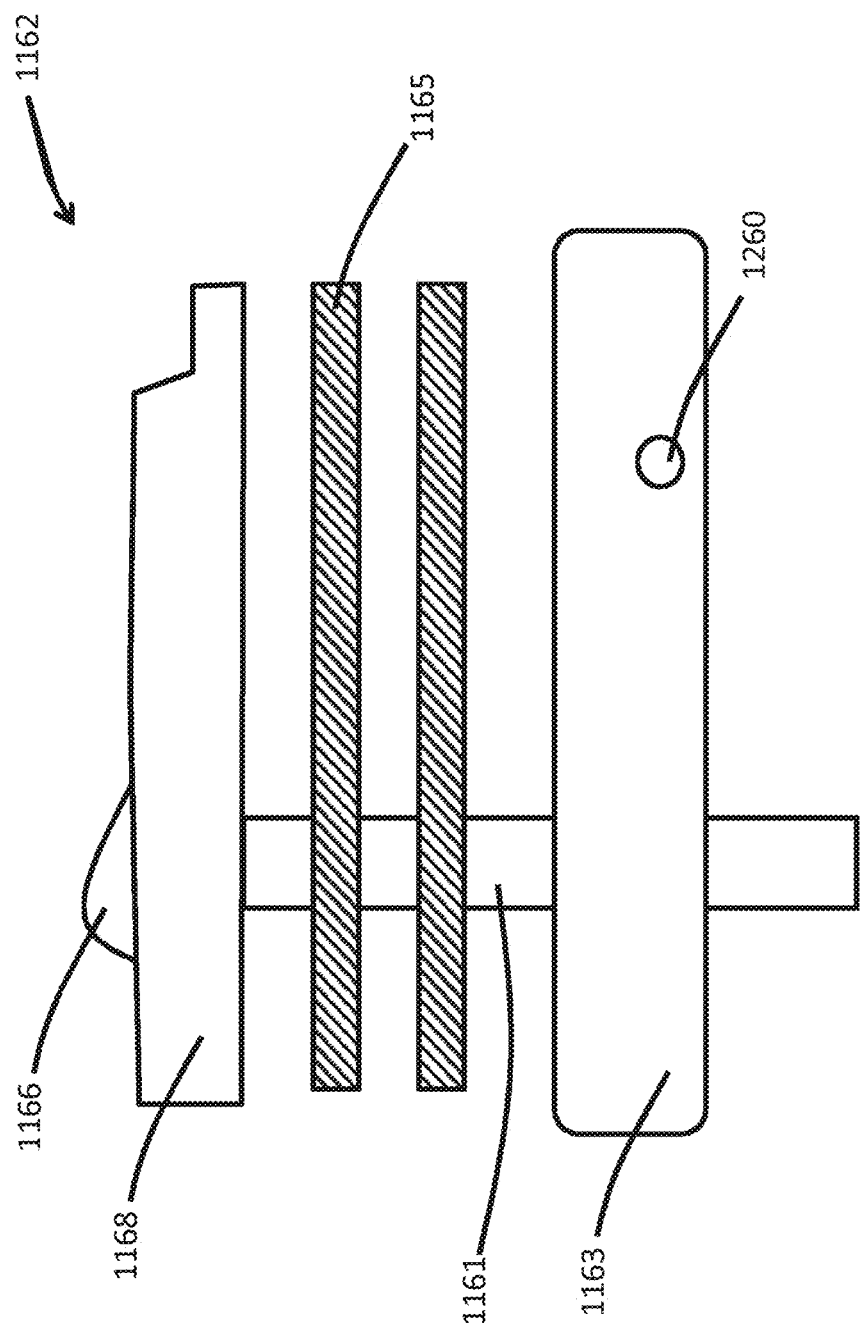
FIG. 13 illustrates an exploded side view of a canister bulkhead.

FIG. 13 shows schematically an exploded side view of the canister bulkhead 1162. The canister bulkhead 1162 can include a top tray 1168 configured to receive the pump assembly 1150. The canister bulkhead 1162 can include a bottom tray 1163. One or more filters 1165 can be housed between the top and bottom trays 1168, 1163. The filters 1165 and the bottom tray 1163 can include a through hole to allow an exudate outflow tube 1161 to pass through the filters 1165 and the bottom tray 1163 to reach the interior space of the canister 1160. The top tray 1168 can include the arm 1166 that activates the seating switch 1404 of the pump assembly 1150 to change the flow path of gas through the pump assembly 1150 when the pump assembly 1150 is seated onto the canister bulkhead 1162, as described above. The top surface of the top tray 1168 can include one or more grooves or channels (not shown) that are configured to direct wound exudate into the canister 1160. The exudate outflow tube 1161 can extend from the top tray 1168 into the interior space of the canister 1160. The bottom tray 1163 can include one or more vents 1260 that provide a flow pathway for air within the canister to reach the pump assembly 1150, thereby allowing the pump assembly 1150 to draw air out of the canister 1160 through the filters 1165 to create a negative pressure within the canister 1160 that draws wound exudate from the dressing 1180 into the canister 1160.

Figure 14:
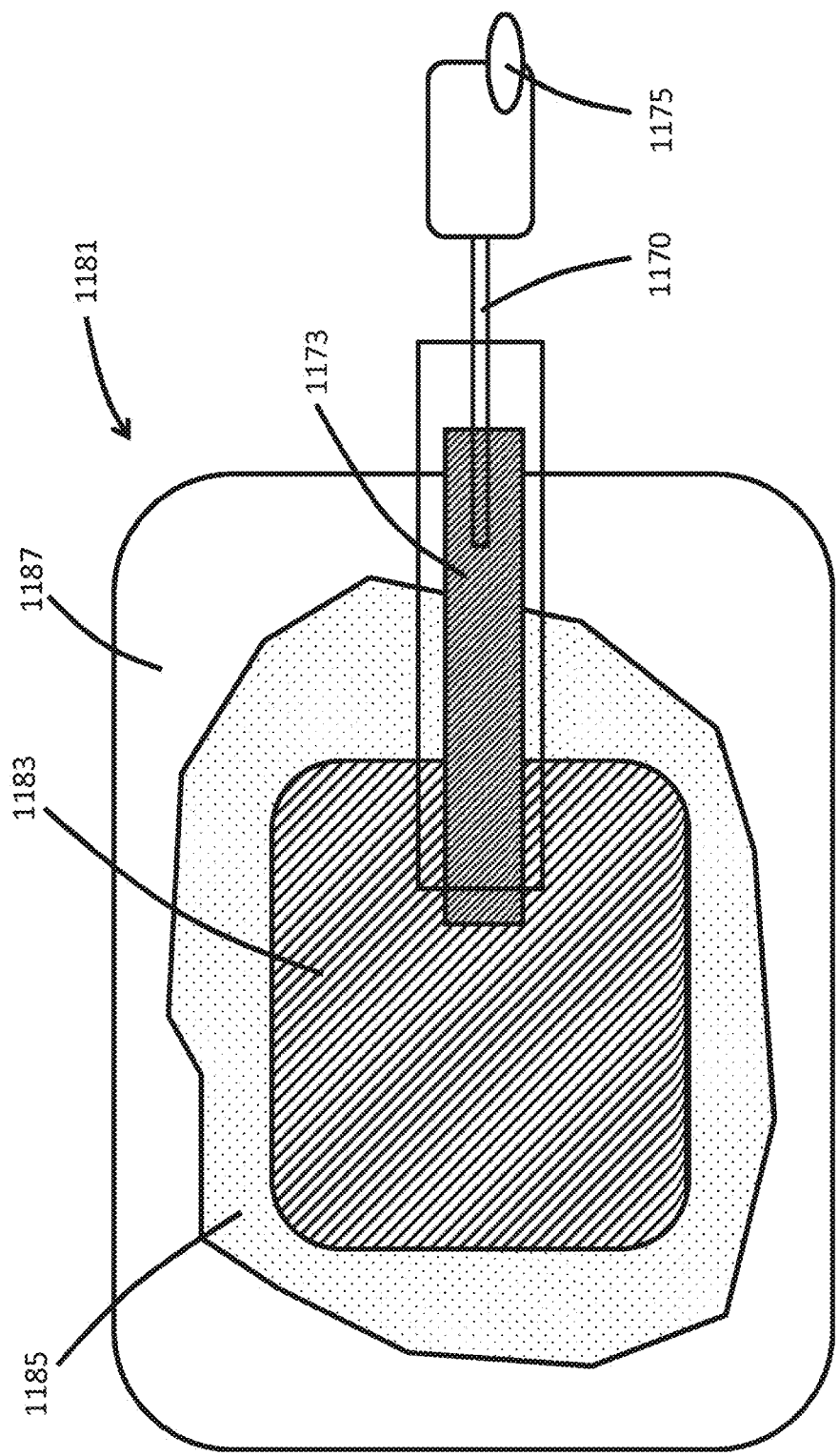
FIG. 14 illustrates a top view of a canister-mode dressing.

FIG. 14 shows an embodiment of the canister-mode wound dressing 1181 that can be used with the pump assembly 1150 when the pump assembly 1150 is seated onto the canister bulkhead 1162 (i.e., canister mode). The canister-mode dressing 1181 can include a wound contact layer 1185, for example Sontara produced by DuPont, to be placed over the wound, the pressure dispersion layer 1183 (or wound filler 130) that may be placed over the wound contact layer within the wound, a transparent backing layer 1187 disposed over the pressure dispersion layer 1183, and the flexible bridge 1173. In some embodiments, the flexible bridge 1173 comprises an adhesive to form a seal over an opening formed in the backing layer 1187. The adhesive may be provided on an underside of the flexible bridge 1173 beneath the distal end of the spacer material. An adhesive may also or alternatively be provided on an underside of an applicator layer that surrounds the distal end of the flexible bridge 1173, such as described in U.S. Pat. No. 8,801,685, the entirety of which is hereby incorporated by reference. The components of the canister-mode dressing 1181 can be separate components that are assembled together to dress the wound. Each of these components may be provided or packaged separately or together, and in some embodiments may be separately inserted into or over the wound. In some embodiments, two or more of the components of the canister-mode dressing 1181 can be pre-assembled with one another or manufactured as a single unit.

In some embodiments, components of any of the above-described TNP systems can be packaged together or separately. For example, in addition to packaging components of the canister-mode dressing together as described above, components of the canisterless-mode dressing (e.g., the dressing 1182, the flexible connector 1172, the conduit adapter 1190 and/or the pump connector 1300) can be packaged together, either separately or with the components of the canister-mode dressing and/or the pump assembly. The pump assembly 1150 can be packaged together or separately from either or both of the canister-mode dressing 1181 and the canisterless-mode dressing 1182.

One embodiment for treating a single patient utilizing the above embodiments will now be described. A wound can be dressed with a canister-mode dressing 1181 by positioning the wound contact layer 1185 into the wound in direct contact with the wound tissue. The pressure dispersion layer 1183, such as wound filler foam 130, can be cut to size and placed within the wound bed on top of the wound contact layer 1185. The backing layer 1187 or drape can be placed over the wound filler. A distal end of the flexible bridge 1173 can be attached over a hole made in the backing layer 1187. A proximal end of the flexible bridge 1173 can include a connection feature 1175, as described above with regard to FIG. 60. The connection feature 1175 can be inserted into the conduit adapter 1190 (as shown in FIG. 5A for a yellow-color-coded canisterless-mode dressing 1182) to connect the flexible bridge 1173 to the pump assembly 1150. In some arrangements, the connection feature 1175 can be pre-assembled with the conduit adapter 1190, linking the flexible bridge 1173 together with the conduit adapter 1190. The flexible bridge 1173 can include an open cell foam. The pressure distribution layer 1183 can be disposed at the wound-side face of the flexible bridge 1173. The pump assembly 1150 can be seated onto the bulkhead of the canister 1160 to establish a flow path between the pump assembly 1150 and the interior space of the canister 1160, as described previously. The pump assembly 1150 can provide negative pressure and draw wound exudate to the canister 1160. The pump assembly 1150 can continue to be used with additional canisters 1160 and/or canister-mode wound dressings 1181A until a desired level of healing is reached. The same pump assembly 1150 can be used with the canisterless-mode dressing 1182 by removing the pump assembly 1150 from the canister 1160 and connecting the pump assembly 1150 to a conduit adapter 1190 connected to a canisterless-mode dressing 1182, as described above.

In some embodiments, one or more alarms can be programmed into the processor of the pump assembly 1150. The pump assembly 1150 can be operated in patient mode, which can allow a user a limited number of selections to adjust operation of the TNP system, or in clinician mode, which can allow the user an expanded number of selections to adjust operation of the TNP system 1100. The pump assembly 1150 can have a battery level indicator. The pump assembly 1150 can have an inactive mode that allows the pump assembly 1150 to be paused for a period of time, such as 30 minutes or another suitable period of time. The inactive mode can allow the operation of the pump assembly 1150 to be temporarily suspended without causing one or more alarms to be activated.

In some embodiments, the pump assembly 1150 can implement play/pause functionality that starts/pauses provision of negative pressure. Play/pause functionality can be activated by a user, such as via operating one or more elements of the user interface (for instance, one or more buttons described herein). In addition or alternatively, play/pause functionality can be activated by the TNP system automatically, such as by the one or more controllers, in response to detecting one or more conditions during operation of the TNP system. For example, the TNP system can detect presence of a leak in the fluid flow path that prevents the TNP system from achieving the negative pressure set point at the wound. Such detection can be performed based on monitoring flow in the fluid path in relation to one or more flow thresholds while monitoring pressure in relation to the set point. Flow can be monitored directly, such as by a flow sensor, or indirectly, such as by measuring and/or monitoring the duty cycle of the pump. Leaks can be detected when the monitored flow reaches or exceeds a particular flow threshold and the monitored pressure has not reached the set point. The TNP system can pause operation of the pump and indicate presence of the leak to the user. After the user addresses the cause of the leak (such as, fixes a poor seal between the wound dressing and the wound), the user can restart operation of the pump or the pump can restart its operation automatically, such as after expiration of a duration of time. Further details of pressure control and determination of one or more operating conditions are found in U.S. Pat. No. 8,734,425, filed on Sep. 16, 2011, and in U.S. Pat. No. 8,905,985, filed on Nov. 2, 2011, and in U.S. Pat. No. 9,737,649, filed on May 13, 2014, and in U.S. patent application Ser. No. 15/500,495, filed on Jan. 30, 2017, each of which applications is incorporated in its entirety by reference herein.

In some embodiments, the TNP system 1100 can generate an inactivity alarm when the TNP system 1100 has been powered on for a certain duration of time without receiving user input. This alarm can be suppressed when an inactive mode (as described herein) is selected or enabled. When the TNP system 1100 is programmed to operate in inactive mode (e.g., to allow the patient to bathe), inactivity detection can be suspended or suppressed for a particular period of time, such as 30 minutes.

Figure 15A:
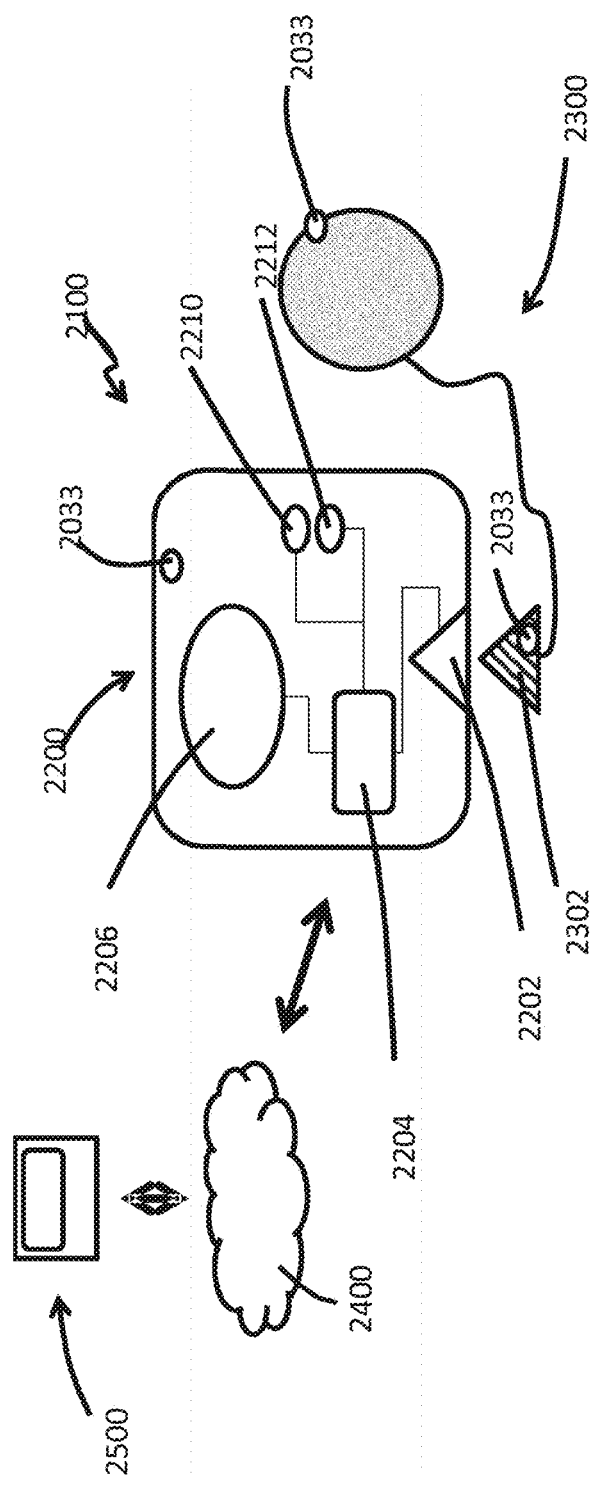
FIG. 15A illustrates a schematic diagram of a system for automating activation or operation of a medical device according to some embodiments.

FIG. 15A shows an illustrative, non-limiting embodiment of a device activation system 2100 that includes a medical device 2200 and a patient-contacting disposable 2300. The medical device 2200 can have a connector port 2202 that connects with a corresponding connector 2302 of the patient-contacting disposable 2300. The system 2100 can be configured so that connection of the patient-contacting disposable 2300 with the medical device 2200 automatically activates or alters the operation of the medical device 2200. For example, the medical device 2200 can be arranged such that connection of a connector 2302 with the connector port 2202 powers on the medical device 2200. In some embodiments, power to the device 2200 is latched on in the device 2200 after the connector 2302 is connected to the device 2200 such that the device 2200 remains powered on when the connector 2302 is no longer attached to the device 2200.

The medical device 2200 can include a processor 2204 that controls operation of a component 2206 (e.g., a motor) of the medical device 2200. In some embodiments, the medical device 2200, the connector 2302, or the patient-contacting disposable 2300 can include one or more sensors 2033. In some embodiments, the sensors 2033 can configure and change operation of the medical device 2200. For example, the sensor 2033 can be disposed on the patient-contacting disposable 2300 and can transmit information to the processor 2204 when the patient-contacting disposable 2300 is connected to the medical device 2200, to automatically configure the operational settings of the medical device 2200 based on the information transmitted to the processor 2204 by the sensor 2033. In some embodiments, the sensors can be a temperature sensor, a humidity sensor, a movement sensor (e.g., an accelerometer), a vibration sensor, a therapy pressure sensor, an ambient pressure sensor. The sensor 2033 can allow monitoring of the patient environment, monitoring of the medical device 2200 environment, or monitoring of both the patient environment and the medical device 2200 environment.

As discussed herein, connection of the connector 2302 to the medical device 2200 can inform the medical device 2200 of one or more characteristics of the wound dressing component associated with the connector 2302. The medical device 2200 can automatically adjust the operational parameter of the device 2200 based on the one or more characteristics. In some embodiments, the connector 2302 can be associated with a canister for collecting wound exudate, and the connection of the connector 2302 to the medical device 2200 can inform the medical device 2200 of the volume capacity of the canister. The medical device 2200 can adjust an operational parameter such as an alarm alerting that the canister is full or a value of negative pressure to supplied by the medical device 2200.

In the illustrated embodiment of FIG. 15A, the medical device 2200 is depicted as being configured to connect with a single patient-contacting disposable 2300. As discussed herein, in some embodiments the medical device 2200 can be connected to more than one patient-contacting disposable 2300.

FIG. 15B shows an embodiment of the medical device 2200A that includes a Y-connect feature 2305 that can be used to connect multiple patient-contacting disposables 2300 to the medical device 2200A. The medical device 2200A can be similar to the medical device 2200 except as described differently below. The features of the medical device 2200A can be combined or included with the medical device 2200 or any other embodiments disclosed herein. For the sake of clarity, FIG. 15B illustrates only a component 2206A (e.g., a negative pressure source) and Y-connect feature 2305 of medical device 2200A. However, the medical device 2206A shown in FIG. 15B can include one or more of the additional features shown in FIG. 15A, as discussed herein. In some embodiments, the medical device 2200A can be configured so that the medical device 2200A does not operate unless all the appropriate patient-contacting disposables 2300 are connected to the medical device 2200A.

The component 2206A can be disposed within a housing 2201 of the medical device 2200. As shown in FIG. 15B, the Y-connect feature 2305 can be arranged such that the trunk of the Y-connect feature 2305 is in fluid communication with a negative pressure source 2206A of the medical device 2200A. In the illustrated embodiment, the two branches of the Y-connect feature 2305 can provide a first connector port 2202' and a second connector port 2202", each of which can be in fluid communication with a patient-contacting disposable 2300 such that two patient-contacting disposables 2300 can be fluidically connected to the negative pressure source 2206A of the medical device 2200A.

As shown in FIG. 15B, the first and second connector ports 2202', 2202" can be disposed on the housing 2201 of the medical device 2200. In the illustrated embodiment, the Y-connect feature 2305 is depicted as being disposed entirely within the housing 2201 of the medical device 2200. In some embodiments, at least a portion of the Y-connect feature 2305 can extend from the housing 2201. For example, the branch point of the Y-connect feature 2305 can be disposed outside of the space enclosed by the housing 2201 rather than inside the housing 2201 as shown in FIG. 15B. In some embodiments, the branch point is disposed within the housing 2201 while the connector ports 2202', 2202" are disposed outside of the housing 2201. In some embodiments, the Y-connect feature can be attached to the housing, such as by extending from an outer surface of the housing. An example of a medical device 2200A that may operate with two patient-contacting disposables 2300 connected to the medical device 2200 is the PICO 7Y™ system sold by Smith & Nephew. In some embodiments, the Y-connect feature 2305 is disposed within the medical device 2200A, and the medical device 2200A can include valves or regulators 2307 that open and close to control which branch or branches of the Y-connect feature 2305 are in fluid communication with the component 2206A of the medical device 2200A.

In some embodiments, the medical device 2200A can be configured such that each of the branches of the Y-connect feature 2305 is configured to allow the medical device 2200A to be used with two different types of patient-contacting disposables 2300. For example, the medical device 2200A can be used with a canister-mode dressing 3181 (FIG. 18B) connected to the first branch of the Y-connect feature 2305 and a canisterless-mode dressing 3182 (FIG. 18A) connected to the second branch of the Y-connect feature 2305, as discussed herein. In some embodiments, the two branches of the Y-connect feature 2305 can connect to the same type of dressing. For example, the Y-connect feature 2305 can be configured such that the medical device 2200 can be used with two canisterless-mode dressings 3182 or with two canister-mode dressings 3181. In some embodiments, one or more optional valves and regulators 2307 are configured to deliver a first mode of negative pressure to the first connector port 2202' and a second mode of negative pressure to the second connector port 2202". The valves or regulators 2307 can be configured so that a single negative pressure source 2206A applies the appropriate negative pressure to a canisterless-mode dressing 3182 (FIG. 18A) connected to the first connector port 2202', while also applying the appropriate negative pressure to a canister-mode dressing 3181 (FIG. 18B) connected to the second connector port 2202". The Y-connect feature 2305 and the valves or regulators 2307 can be disposed within the connector 2302. In some embodiments, the connector 2302 can include a Y-connect feature 2305 that is configured such that the base of the Y-connect feature 2305 is coupled to the connector port 2202 and each the branches of the Y-connect feature 2305 is adapted to be connected to a patient-contacting disposable 2300.

FIG. 15C shows an embodiment of the medical device 2200B that includes multiple, spaced-apart connector ports 2202', 2202" that are each connected to a separate component 2206A, 2206B of the medical device 2200B. In the illustrated embodiment, the medical device 2200 has two spaced-apart connector ports 2202', 2202". In some embodiments, the medical device can have more than two (e.g., three, four, more than four) spaced-apart connector ports 2202. The medical device 2200B can be similar to the medical device 2200A except as described differently below. The features of the medical device 2200B can be combined or included with the medical device 2200A or any other embodiments disclosed herein. As shown in FIG. 15C, the medical device 2200B can include a first component 2206A (e.g., a negative pressure source) that is connected to a first connector port 2202' by a first flow path 2309. The medical device 2200B can include a second component 2206B (e.g., an irrigation source) that is in fluid communication with a second connector port 2202" through a second flow path 2311. Negative pressure can be applied to the wound through the first connector port 2202' and irrigation can be provided to the wound through the second connector port 2202". Irrigation can include introducing an irrigation fluid into the wound. The irrigation fluid can be a liquid or a gas. In some embodiments, a positive pressure source is used to introduce the irrigation fluid into the wound. The irrigation source can be referred to herein as a positive pressure source. However, the irrigation source need not necessarily be a positive pressure source.

In some embodiments, the medical device 2200B can be configured so that the medical device 2200B does not operate unless all the appropriate patient-contacting disposables 2300 are connected to the medical device 2200B. For example, the medical device 2200B can have a first connector port 2202' for applying suction to the wound and a second connector port 2202" for applying irrigation to the wound, with the medical device 2200B being configured to not operate in the absence of an appropriate patient-contacting disposable 2300 being connected to each of the first and second connector ports 2202', 2202". In some embodiments, the first component 2206A can be a negative pressure source configured for use with a canisterless-mode dressing 3182 (FIG. 18A) and the second component 2206B can be a negative pressure source configured for use with a canister-mode dressing 3181 (FIG. 18B). As shown in FIG. 15C, a first and second valve or regulator 2307', 2307" can be interposed between the first and second connector port 2202', 2202" and the respective component 2206A, 2206B. In some embodiments, the first component 2206A is a first negative pressure source configured to deliver a first mode of negative pressure, and the second component 2206B is a second negative pressure source configured to deliver a second mode of negative pressure. In some embodiments, the medical device 2200B is configured such that in use a canisterless-mode dressing 3182 (FIG. 18A) can be connected to the first connector port 2202', and a canister-mode dressing 3181 (FIG. 18B) can be connected to the second connector port 2202". As discussed herein, the medical device 2200, 2200A, 2200B can detect the type of patient-contacting disposable 2300 (e.g., wound dressing) that is connected to any of the connector ports 2202 of the device 2200 to adjust the therapy or settings of the device 2200 accordingly. In some embodiments, the device 2200, 2200A, 2200B can adjust the alarm strategies or alarm thresholds according to the patient-contacting disposable(s) 2300 that are connected to the device 2200, 2200A, 2200B, as discussed herein. Alarm strategies or alarm thresholds can be directed to alerting a user or clinician of leaks, blockages, saturation of a dressing, or a full canister.

Referring again to FIG. 15A, the patient-contacting disposable 2300 can be configured in manufacture to activate (e.g., power up) the electrical medical device 2200 when the disposable 2300 is connected to the device 2200, 2200A, 2200B. In alternative embodiments, the patient-contacting disposable 300 can be factory configured to prescribe the therapy setting that the electrical medical device 2200 delivers. In some embodiments, connection of the patient-contacting disposable 2300 to the medical device 2200 turns the device 2200 on or takes the device 2200 from a state of dormancy to an active state. The active state can allow the user to initiate therapy or make changes to the therapy setting before initiating therapy or during therapy.

In some embodiments, connection of the connector 2302 with the connector port 2202 can initiate a lifetime timer for the medical device 2200. In some arrangements, the lifetime timer is configured such that after the duration of the lifetime timer expires, the medical device 2200 is powered off and cannot be powered on again. In some variants, the connector 2302 can be configured to inform the medical device 2200 of the type or identity of the patient-contacting disposable 2300 that is connected to the medical device 2200. In some embodiments, the connector 2302 can be configured to inform the medical device 2200 of one or more characteristics (e.g., lot number, product identification number) of the wound dressing that is associated with the connector 2302 that is connected to the connector port 2202. In certain arrangements, the medical device 2200 can begin a timer that is specific for the patient-contacting disposable 2300 connected to the connector port 2202 of the medical device 2200. For example, if the patient-contacting disposable 2300 is performing a filtering or cleansing function, the medical device 2200 can begin a timer that approximates the lifespan the patient-contacting disposable 2300 will remain effective at performing the filtering or cleansing function. Once the patient-disposable lifespan timer expires, the medical device 2200 can be configured to alert the user of the need to change the patient-contacting disposable 2300. In some embodiments, the medical device 2200 can be disabled until the medical device 2200 detects that the patient-contacting disposable 2300 has been changed.

With continued reference to FIG. 15A, the medical device 2200 can include a processor 2204 that controls operation of a component 2206 (e.g., a motor) of the medical device 2200. The processor 2204 can power on the medical device 2200 when the processor 2204 detects that a connector 2302 of a patient-contacting disposable 2300 has been connected to the connector port 2202 of the medical device 2200. The connector 2302 of the patient-contacting disposable 2300 can be configured to inform the processor 2204 of identification information for the patient-contacting disposable 2300 that is connected to the connector port 2202. In some embodiments, the identification information can include: the model or type of the patient-contacting disposable, the lot number of the patient-contacting disposable, the patient information of a patient associated with the patient-contacting disposable, the alarm settings to use with the patient-contacting disposable, the therapy regime to use with the patient-contacting disposable.

In some embodiments, disconnecting the patient-contacting disposable 2300 from the medical device 2200 can automatically deactivate the medical device 2300. For example, disconnection of the connector 2302 from the connector port 2202 can cause the processor 2204 to power down the medical device 2200. In some variants, disconnection of the connector 2302 from the connector port 2202 can trigger the medical device 2200 to transmit or upload patient data to an intermediary server 2400. The intermediary server 2400 can be arranged to allow a remote computer 2500 to access or download the patient information from the intermediary server 2400. In some embodiments, the intermediary server 2400 is a cloud-based memory storage service. In some embodiments, the remote computer 2500 allows the user or a health care professional to access the patient information uploaded to the intermediary server 2400 by the medical device 2200. In some embodiments, connecting the connector 2302 to the device 2200 causes the device 2200 to transmit connector identity data to the intermediary server 2400, thereby informing the intermediary server 2400 of the identity of the connector that is connected to the device 2200. In some embodiments, connecting the connector 2302 to the device 200 causes the device 2200 to receive therapy data from the intermediary server 2400, thereby informing device 2200 of the operational settings the device 2200 should use for the connector 2302 that is connected to the device 2200.

In some embodiments, the connector 2302 can be configured such that a unique disposable identification information can be communicated to or from the medical device 2200 or the intermediary server 2400. In some embodiments, the unique disposable identification information can be used to allow traceability and compliance tracking of the patient-contacting disposable 2300 or the medical device 2200, which can be important for compliance with medical device monitoring regulations. In some embodiments, the therapy set up for the medical device 2200 can be sent to the intermediary server 2400, allowing a prescribing doctor to confirm a nurse has applied the correct patient-contacting disposable 2300. The connector 2302 can inform the medical device 2200 of the compliance conditions to be met so that all alerts are triggered accordingly. For example, the connector 2302 can inform the medical device 2200, 2200A, 2200B that the patient is supposed to be using the particular dressing 2300 at a negative pressure of 120 mmHg for 22 hours per day. When the dressing 2300 is connected to the device 2200, 2200A, 2200B, if the patient does not achieve this prescribed therapy (e.g., 120 mmHg for 22 hours/day), the medical device 2200 can signal an alert, store information regarding the compliance failure, and/or transmit information regarding the compliance failure to the user or clinician. As disclosed herein, the medical device 2200, 2200A, 2200B can determine alarm thresholds based on the type of patient-contacting disposable 2300 connected to the medical device 2200. For example, connection of a first type of dressing (e.g., foam dressing) can inform the user to change the dressing after a first time span (e.g., 3 days) while connection of a second type of dressing (e.g., PICO™ dressing) can inform the user to change the dressing after a second time span (e.g., 7 days).

In some embodiments, disconnection of the connector 2302 from the device 2200 can be configured to automatically stop therapy and provide messaging to the user via an output indicator (e.g., display screen, speaker). The device 2200 may inform the user of the maximum allowable disconnection time based on a default setting or alternatively based on a therapy guideline predefined by a clinician. On expiry of the time limit, the device 2200 may alert the user to reconnect the connector 2302 to the device 2200 and resume therapy.

In some embodiments, the connector 2302 may contain a power source (e.g., a battery) and an alert system. The power source of the connector 2302 can be configured to provide power to the connector 2302 when the connector 2302 is disconnected from the device 2200. The power source can be charged by the device or wirelessly (e.g., inductively). The power source and alert system of the connector 2302 can be configured to provide an alert to the user when the connector 2302 is disconnected from the medical device 2200 such as when the user is bathing. The connector 2302 can alert the user as to when to reconnect to the device 2200 and restart therapy. The connector 2302 can include a memory device to maintain a record of the time that therapy has been applied and adjust a restart therapy alarm setting accordingly. The memory device of the connector 2302 may update and compare data with a memory log of the device 2200 when connected to the device 2200. In this way, both the device 2200 and the connector 2302 may alarm at the same time point to restart therapy. In some embodiments, the system 2100 can be configured to allow a user to select a pause therapy time period from available periods via a user interface (e.g., GUI) of the device 2200. The device 2200 can configure a time delay for the alarm on the connector 2302 to restart therapy.

The medical device 2200 can include an output 2210 that allows the medical device 2200 to provide information to the user. The output 2210 can be a visual output (e.g., a display) or an audio output (e.g., a speaker). The output 2210 can be an alarm that alerts the user of an event that requires the user's attention. The alarm could be related to a low battery power of the device, a suspected malfunction (e.g., a blockage, a leak), or some other event requiring the user's attention. The alarm settings can be tailored to the patient-contacting disposable 2300 that is connected to the medical device 2200. For example, the threshold for activating the alarm can be different for a first patient-contacting disposable compared to a second patient-contacting disposable. In some arrangements, the medical device 2200 can automatically set an alarm parameter or threshold value based on the identity of patient-contacting disposable 2300. The operation mode of the medical device 2200 (including the alarm thresholds of the medical device 2200) can be adjusted or modified based on the type of patient-contacting disposable 2300 is connected to the medical device 2200. In some embodiments, an alarm threshold for detecting a leak or blockage in the system can be adjusted based on the type of patient-contacting disposable 2300 connected to the medical device 2200. For example, the medical device 2200 can include a Y-connect feature 2305 (FIG. 15B) for treatment of multiple wounds, and the medical device 2200 can alter or modify detection of one or more conditions, such as blockages, leaks, canister full condition, and the like. The medical device 2200 can be configured such that when the medical device 2200 detects multiple patient-contacting, disposables 2300 are connected to the medical device 2200 the medical device 2200 can adjust one or more of various thresholds described above. For example, connecting multiple patient-contacting disposables 2300 to the medical device 2200 can cause the medical device 2200 to decrease sensitivity of blockage detection by increasing the blockage threshold. The blockage threshold can be increased by a suitable amount, such as doubled.

The medical device 2200 can include an input 2212 that allows a user to input information to the medical device 2200. The input 2212 can be a button that allows a user to select options from a user interface of the medical device 2200. The medical device 2200 can tailor the available submenus or selections of the user interface based on the identity of patient-contacting disposable 2300 that is connected to the connector port 2202 of the medical device 2200. For example, the submenus or options for a user interface of the medical device 2200 can be different when a first patient-contacting disposable is connected to the medical device 2200 compared to the submenus and options available for the user interface when a second patient-contacting disposable is connected to the device 2200. In some arrangements, the medical device 2200 can automatically modify the user interface options or submenus based on the identity of patient-contacting disposable 2300 connected to the device 2200.

In some arrangements, the medical device 2200 can detect the identity of the connector 2302 attached to the connector port 2202 by electrical connectivity. In the case of activation of the device 2200, a circuit, or preferable two circuits, can be sufficient to inform the device 2200 of the identity of the patient-disposable 2300 connected to the connector port 2202 of the device 2200. Circuit could include one or more resistors, capacitors, or the like in the connector 2302 whose resistance, capacitance, or the like is detected by the medical device 2200. For example, the medical device 2200 can detect different resistance values of the one or more resistors and determine the therapy and mode of operation of the medical device based on the type of connector 2302 that is connected to the medical device 2200. In some embodiments, the connector 2302 may include one or more active electrical components. For example, the connector 2302 can include a microcontroller and a memory device to store different information (e.g., mode, calibration, part numbers, batch number, sensor data, status of one or more valves or actuators to control flow or leak). The medical device 2200 can communicate with the patient-contacting disposable 2300 to transfer data, power, or both data and power to the patient-contacting disposable 2300. Communications can transfer power and/or data, such as using a protocol, for example, serial, inter-integrated circuit (I2C), serial peripheral interface (SPI), low powered wireless (e.g., low-power wide-area network). Power can be provided directly, (such as, through the connector ports 2202 and 2302), inductively, through a protocol, or the like. The disposable 2300 can include a rechargeable power source. In some cases, data communications between the device 2200 and disposable 2300 may be encrypted. In some arrangements, a radio-frequency identification (RFID) device may be embedded in the connector 2302 of the disposable 2300. On connection of the connector 2302 to the device 2200, the RFID is energized by the device 2200 and information is sent wirelessly to the electrical device 2200, configuring the processor 2204 in the electrical device 2200 accordingly. The electrical device 2200 can then ask the user to confirm that the settings are correct before allowing the therapy to be activated.

Figure 16:
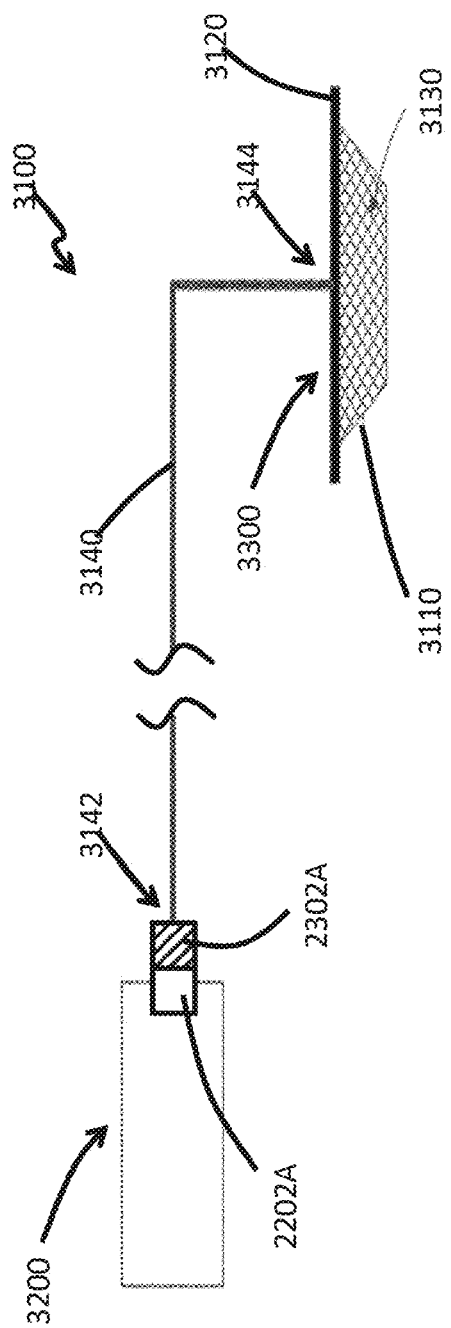
FIG. 16 shows a schematic diagram of a negative pressure wound therapy system having an automated system for activation or operation of the pump assembly.

As discussed, some embodiments disclosed herein relate to systems and methods of treating a wound with reduced pressure. FIG. 16 illustrates a schematic diagram of a NPWT system 3100. The NPWT system 3100 can include a wound filler 3130 placed inside a wound cavity 3110. The wound cavity 3110 can be sealed by a wound cover 3120. In some embodiments, one or more of the wound filler 3130, the wound cover 3120, or any other component, such as a contact layer (not shown), make up a wound dressing 3300. The NPWT system 3100 can include a negative pressure wound therapy apparatus or a pump assembly 3200 configured to provide reduced pressure to the wound. For example, a conduit 3140 having at least one lumen can provide a fluid flow path between the pump assembly 3200 and the wound. The conduit 3140 can have a pump end 3142 that is fluidically connected to the pump assembly 3200 and a wound end 3144 that provides fluid communication to a space underneath the wound cover 3120. For example, the conduit may connect the wound cover through a port positioned over an opening in the wound cover, or the conduit may be positioned underneath the wound cover. The conduit 3140 can communicate a negative pressure at the pump end 3142 to the wound end 3144.

As shown in FIG. 16, the wound dressing 3300 can have a connector 2302A at the pump end 3142 of the conduit 3140. The connector 2302A can be similar to the connector 2302 except as described differently below. The features of the connector 2302A can be combined or included with the connector 2302 or any other embodiments disclosed herein. The connector 2302A can be arranged to form a fluidic connection with a connector port 2202A of the pump assembly 3200. The connector port 2202A can be similar to the connector port 2202 except as described differently below. The features of the connector port 2202A can be combined or included with the connector port 2202 or any other embodiments disclosed herein. The pump assembly 3200 can include a processor that activates or operates the pump assembly 3200 upon connection of the connector 2302A with the connector port 2202A, as described above with regard to the medical device 2200 of FIG. 15A.

The NPWT system 3100 can be configured such that the connector 2302A informs the NPWT system 3100 of the type of wound dressing 3300 that is connected to the pump assembly 3200. The NPWT system 3100 can automatically adjust one or more operational parameters of the pump assembly 3200 based on the type of connector 2302A that is connected to the connector port 2202A. In some embodiments, the NPWT system 3100 can prescribe a therapy regime of NPWT based on the type of connector 2302A that is connected to the connector port 2202A. The NPWT configuration of therapy may include setting the vacuum level delivered to the wound, selecting intermittent or variable pressure settings (e.g., time and pressure parameters), setting the intensity of therapy or rate at which the negative pressure is varied, setting alarm thresholds for alerting the user of a blockage or leakage at the wound, specifying the number of wounds or the total wound volume of the wound(s) that are connected to the pump assembly 3200. In some arrangements, the alarm thresholds can be set based on the number of wounds, or the wound volume of the wound(s), connected to the pump assembly 3200. The NPWT system 3100 can include a timer to track or limit the total duration of therapy. The system 3100 can include an end of life parameter that determines when the pump assembly 3200 goes into a state of dormancy or is no longer active for use.

FIGS. 17A-17B illustrate that the NPWT system 3100 can be configured to operate with and without a canister (e.g., canister and canisterless modes). In particular, the same pump assembly 3200 can be used in both canister and canisterless modes. FIG. 17A shows an embodiment of the TNP system 3100 that has a wound dressing 3180A connected directly to the pump assembly 3200 (e.g., canisterless mode). FIG. 17B shows an embodiment of the TNP system 3100 that has a canister 3160 interposed between a wound dressing 3180B and the pump assembly 3200 (e.g., canister mode). At the beginning of the application of negative pressure wound therapy to a wound, when the wound is in the early stages of the healing process and exudes a significant volume of exudate, the reduced pressure wound therapy system may operate with a canister. In this mode of operation, the negative pressure wound therapy system may operate with a foam or gauze RENASYS™ dressing sold by Smith & Nephew or any other suitable dressing. Operation of the reduced pressure wound therapy system with a canister may sometimes be referred to herein as "RENASYS™", "RENASYS™-mode", or derivatives thereof. As the wound is progressing through the healing process and is starting to exude a smaller volume of exudate, the canister may be removed and the negative pressure wound therapy system may operate with an absorbent dressing, such as the PICO™ dressing sold by Smith & Nephew or any other suitable dressing that retains the wound exudate within the dressing. Further details of absorbent dressings such as the PICO™ dressing are found in U.S. Pat. No. 9,061,095, filed on Apr. 21, 2011, and incorporated in its entirety by reference herein. Operation of the reduced pressure wound therapy system without a canister may sometimes be referred to herein as PICO™, "PICO™-mode", or derivatives thereof.

Referring to FIG. 17A, the pump assembly 3200 can have a connector port 2202A that allows the pump assembly 3200 to be connected to a canisterless wound dressing 3180A. The cansiterless wound dressing can include a connector 2302C that forms a fluidic connection with the connector port 2202A. Connection of the connector 2302C can activate the pump assembly 3200 or modify the operation of the pump assembly 3200, as described previously. The NPWT system 3100 can be configured so that connection of the connector 2302C to the connector port 2202A informs the pump assembly 3200 that a cansiterless dressing 3180A has been connected to the pump assembly 3200. Further details of connector arrangements that can inform a NPWT pump assembly whether a canister or canisterless mode dressing is attached to the pump assembly are found in International Application No. PCT/US18/18446, entitled "NEGATIVE PRESSURE WOUND THERAPY APPARATUSES AND METHODS FOR USING THE SAME," filed on Feb. 15, 2018, and incorporated in its entirety by reference herein.

Referring to FIG. 17B, the pump assembly 3200 can have a connector port 2202A that allows the pump assembly 3200 to be connected to a canister-mode wound dressing 3180B. The canister 3160 can include a connector 2302D that forms a fluidic connection with the connector port 2202A, as shown in FIG. 17B. Connection of the connector 2302D can activate the pump assembly 3200 or modify the operation of the pump assembly 3200, as described previously. The NPWT system 3100 can be configured so that connection of the connector 2302D to the connector port 2202A informs the pump assembly 3200 that a canister-mode dressing 3180B has been connected to the pump assembly 3200.

The type of dressing or patient-contacting disposable (e.g., canisterless or canister-mode) can be determined by the NPWT system 3100. After determining the type of disposable connected to the pump assembly 3200, the NPWT system 3100 may further configure or adjust alarm thresholds (e.g., canister full or dressing full) according to thresholds that correspond to the type of disposable that is connected to the pump assembly 3200. In certain arrangements, calibration data for the disposable may be passed to the pump assembly 3200. In some arrangements, other therapies may also be configured. For example, in the case of infusion of a fluid, the dosage may be set, or the volume of fluid delivered can be set, or the pressure of the infused fluid can be set, or the time or rate of fluid infusion can be set. In the case of therapies that deliver ultrasound to the tissue, the parameters of the ultrasound therapy (e.g., power, frequency, duration, pulse timing, and other parameters) can be set by connection of the disposable to the electrical device. In some arrangements, a single device can be capable of delivering any or all or combinations of the aforementioned therapies, and the device can automatically set its operational parameters to deliver the appropriate therapy corresponding to the patient-contacting disposable that is connected to the electrical device. In this way, a user can purchase a single medical device that adjusts its operation based on the patient-contacting disposable that is connected to the medical device.

In some embodiments, encrypted personal identification data may also be transmitted to the medical device for verification of patient data for further download into a remote electronic medical record (EMR). The patient-contacting disposable may have a unique identification number that can be associated to a patient record. The identification code may be passed to the electrical device on connection and logged against the therapy setting device, serial number, location, alarm settings, sensor readings, etc. The data along with further therapy data and compliance data can then be uploaded to a remote EMR.

In certain variants, the disposable or the device can have a sensor (e.g., pressure sensor, flow sensor) or variable performance due to manufacturing tolerances or calibration data for the disposable. The calibration data for the disposable can be passed to the device to adjust settings of the electrical device in order to perform therapy or alerts and alarms. As discussed, in some embodiments, the disconnection of the disposable may shut down the electrical device. Disconnection can also trigger an alarm to alert the user of the disconnection. Disconnection may also trigger an upload of data to a remote database, as discussed previously with regard to FIG. 15A.

One of the advantages of the methods and systems of the present disclosure is that it simplifies the use of the electrical medical device. Also, users can select preconfigured product combinations via selection of a disposable medical device. Human error is reduced in the use of complex user interfaces. Safety and compliance for the patient is improved. Traceability and data capture are improved also. Product malfunction can be linked to a specific lot code of disposable through unique identification numbers, allowing faster or more efficient methods of managing lot recalls.

FIGS. 18A-18B illustrate another example of a TNP system 3100 that uses the same medical device 2200 when the TNP system 3100 operates in either canisterless mode (FIG. 18A) or canister mode (FIG. 18B). The connector 2302E, 2302F can be similar to the connector 2302 except as described differently below. The features of the connector 2302E, 2302F can be combined or included with the connector 2302 or any other embodiments disclosed herein. As shown in FIGS. 18A and 18B, the TNP system 3100 can be configured so that a flow path through the medical device 2200 is modified depending on whether the medical device 2200 is seated onto a bulkhead 3162 of a canister 3160. For example, the medical device 2200 can move fluid along a first flow path 2011 (shown in FIG. 18B) when the medical device 2200 is seated on the bulkhead 3162 and can move fluid along a second flow path 2022 (shown in FIG. 18A) when the medical device 2200 is unseated from the bulkhead 3162, the first flow path 2011 being different from the second flow path 2022.

As shown in FIGS. 18A and 18B, the patient-contacting disposable 2300 can include a dual-lumen conduit 2303 that extends from the connector 2302E, 2302F to the dressing 3182, 3181 portion of the patient-contacting disposable 2300. In some embodiments, a lumen of the dual-lumen conduit 2303 can be used to apply to the wound a negative pressure that is generated by the medical device 2200. In some embodiments, a lumen of the dual-lumen conduit 2303 can be in fluid communication with a pressure sensor. In some embodiments, a lumen of the dual-lumen conduit 2303 can be configured to provide a vent. Further details of connector arrangements that can inform a NPWT pump assembly whether a canister mode dressing 3181 or canisterless mode dressing 3182 is attached to the pump assembly are found in U.S. Provisional Patent Application No. 62/612,263, entitled "NEGATIVE PRESSURE WOUND THERAPY APPARATUSES AND METHODS FOR USING THE SAME," filed on Dec. 29, 2017, and incorporated in its entirety by reference herein.

The patient-contacting disposable 2300 can include an intermediate connection feature 2313 that is disposed between the connector 2302E, 2302F and the dressing 3182, 3181 portions of the patient-contacting disposable 2300. In some embodiments, the intermediate connection feature 2313 can include a one-way valve that is configured to allow the dressing 3182, 3181 to maintain a negative pressure at the wound when the patient-contacting disposable is disconnected from the device 2200. For example, the intermediate connection feature 2313 can include a one-way valve that is actuated or engaged by depressing a button 2315 of the intermediate connection feature 2313. When the one-way valve is actuated, the one-way valve can block the flow path between the portions of the dual lumen conduit 2303 that are disposed on either side of the intermediate connection feature 2313, thereby allowing the dressing 3182, 3181 to maintain negative pressure at the wound when the connector 2302E, 2302F is disconnected from the medical device 2200. This arrangement can allow a negative pressure to be maintained at the wound when the device 2200 is disconnected from the patient-contacting disposable 2300, such as to allow the user to bathe without having the device 2200 connected to the patient-contacting disposable 2300 that is attached to the patient.

In some embodiments, the device 2200, 2200A, 2200B can be configured to suspend alarm notifications when the connector 2302 is disconnected from the device 2200, 2200A, 2200B. In some embodiments, the device 2200 can allow the user to specify the duration of time for which alarm notifications are suspended. In some embodiments, the alarm notifications can be suspended without disconnecting the connector 2302 from the device 2200. For example, if the patient-contacting disposable 2300 informs the device 2200 that the patient-contacting disposable 2300 should be used to apply 80 mmHg of negative pressure to the wound for 20 hours per day, the device 2200 can be configured to suspend alarm notifications during the time the pump of the medical device 2200 is inactive.

While the device activation system 2100 has been described in the context of a connector 2302 that connects to a connector port 2202 of the medical device 2200, in some embodiments a dongle (not shown) can be used to automatically inform the medical device 2200 of the characteristics of the patient-contacting disposable 2300 that is attached to the medical device 2200. In some embodiments, the dongle can be configured to automatically adjust an operational parameter of the medical device 2200, as discussed herein. For example, the medical device 2200 can include a dongle port (not shown) that receives the dongle or the medical device 2200 can have a dongle reader (not shown) that receives data from a dongle that is swiped over the dongle reader. In some embodiments, the dongle is interposed between the connector port 2202 of the device 2200 and the connector portion of the patient-contacting disposable 2300. In some embodiments, the dongle can be provided or sold by itself as a separate connector piece that is plugged into the device 2200 or connected to the connector 2302. In some embodiments, the device activation system 2100 is the dongle itself. The dongle can be provided separately from the wound dressing and pump and is assembled between the wound dressing and the pump to automatically modify one or more operational parameters of the pump when the dongle is connected to or detected by the device 2200.

In some embodiments, the dongle allows a general purpose patient-contacting disposable 2300 to be used with the device 2200 while allowing the operational parameters of the medical device 2200 to be programmed or automatically adjusted as discussed herein. For example, if a clinician wants to prescribe a therapy pressure of 120 mmHg, a dongle can be used to adjust the operation of the device 2200 while allowing a general-purpose patient-contacting disposable 2300 to be used with the device 2200. In this way, inventory management of the patient-contacting disposable 2300 can be simplified.

In some embodiments, the device activation system 2100 can be provided as a kit. The kit can be configured through the connector 2302 or the dongle. The kit can include tubing, a dressing, a canister, a medical device 2200, and any combination thereof. In some embodiments, the connector 2302 or dongle can be a standalone component that configures therapy settings for the system 2100, as discussed herein. For example, the standalone connector 2302 or dongle can be attached to the medical device 2200 or to a general-purpose disposable to configure the therapy settings and duration of therapy.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

Certain embodiments of the disclosure are encompassed in the claims presented at the end of this specification, or in other claims presented at a later date. Additional embodiments are encompassed in the following set of numbered embodiments:

Embodiment 1. A negative pressure wound therapy system comprising:
 a pump assembly; and
 a connector port disposed on the pump assembly, the connector port configured to receive a connector associated with a wound dressing;
 wherein the pump assembly is configured to automatically adjust an operational parameter of the pump assembly based on connecting the connector associated with the wound dressing to the connector port.

Embodiment 2. The negative pressure wound therapy system of Embodiment 1, wherein the connector port is configured such that connection of the connector to the connector port informs the pump assembly of one or more characteristics of the wound dressing or a component associated with the wound dressing.

Embodiment 3. The negative pressure wound therapy system of Embodiment 2, wherein the pump assembly is configured to automatically adjust an operational parameter of the pump assembly based on the one or more characteristics of the wound dressing or the component associated with the wound dressing.

Embodiment 4. The negative pressure wound therapy system of Embodiment 2 or 3, wherein the one or more characteristics of the wound dressing or the component associated with the wound dressing includes the type of wound dressing.

Embodiment 5. The negative pressure wound therapy system of Embodiment 4, wherein the connector port is configured to detect at least whether the wound dressing is a canisterless mode or a canister-mode wound dressing.

Embodiment 6. The negative pressure wound therapy system of any one of Embodiments 2-5, wherein the one or more characteristics of the wound dressing or the component associated with the wound dressing includes calibration information or a lot number of the wound dressing.

Embodiment 7. The negative pressure wound therapy system of any one of Embodiments 2-6, wherein the one or more characteristics of the wound dressing or the component associated with the wound dressing includes a canister full level of a canister associated with the wound dressing.

Embodiment 8. The negative pressure wound therapy system of any one of Embodiments 2-7, wherein the one or more characteristics of the wound dressing or the component associated with the wound dressing is selected from the group consisting of a temperature, humidity level, saturation level and movement of the wound dressing.

Embodiment 9. The negative pressure wound therapy system of any one of the preceding Embodiments, wherein the pump assembly is configured to automatically power on upon connection of the connector with the connector port.

Embodiment 10. The negative pressure wound therapy system of any one of the preceding Embodiments, wherein the pump assembly is configured to select automatically an available option of a user interface of the pump assembly based on the type of connector that is connected to the connector port.

Embodiment 11. The negative pressure wound therapy system of any one of the preceding Embodiments, wherein the operational parameter is selected from the group consisting of: a level of negative pressure, a time duration of negative pressure, a temporal variation of negative pressure, a volume of fluid infused into the wound, a pressure of a fluid infused into the wound, and an alarm setting.

Embodiment 12. The negative pressure wound therapy system of any one of the preceding Embodiments, wherein connection of the connector to the connector port triggers a lifetime timer for the pump assembly.

Embodiment 13. The negative pressure wound therapy system of Embodiment 12, wherein the system is configured such that once a duration of the lifetime timer for the pump assembly expires the pump assembly cannot be powered on again.

Embodiment 14. The negative pressure wound therapy system of any one of the preceding Embodiments, wherein connection of the connector to the connector port triggers a lifetime timer for the wound dressing.

Embodiment 15. The negative pressure wound therapy system of Embodiment 14, wherein the system is configured such that once a duration of the lifetime timer for the wound dressing expires the pump assembly cannot be powered on again until the component of the wound dressing has been disconnected from the pump assembly.

Embodiment 16. The negative pressure wound therapy system of any one of the preceding Embodiments, further comprising the wound dressing comprising the connector configured to connect with the connector port.

Embodiment 17. The negative pressure wound therapy system of Embodiment 16, wherein the wound dressing comprises an ultrasonic transducer, and wherein the pump assembly automatically adjusts an operational parameter of the ultrasonic transducer upon connection of the connector associated with the wound dressing to the pump assembly.

Embodiment 18. The negative pressure wound therapy system of Embodiment 17, wherein the operational parameter of the ultrasonic transducer is selected from the group consisting of: a power of the ultrasonic transducer, a frequency of the ultrasonic transducer, a duration of powering the ultrasonic transducer, and a pulse timing of the ultrasonic transducer.

Embodiment 19. The negative pressure wound therapy system of any one of the preceding Embodiments, wherein the pump assembly is configured such that disconnecting the connector from the connector port deactivates the pump assembly.

Embodiment 20. The negative pressure wound therapy system of any one of the preceding Embodiments, wherein the pump assembly is configured such that disconnecting the connector from the connector port suspends alarm notifications of the pump assembly.

Embodiment 21. The negative pressure wound therapy system of any one of the preceding Embodiments, wherein the pump assembly is configured such that disconnecting the connector from the connector port causes the pump assembly to upload data to a computer server.

Embodiment 22. The negative pressure wound therapy system of any one of the preceding Embodiments, further comprising a plurality of wound dressings each comprising a connector configured to connect with the connector port, wherein each of the connectors is configured to set a different operational parameter of the pump assembly.

Embodiment 23. The negative pressure wound therapy system of any one of the preceding Embodiments, further comprising a Y-connect feature, a trunk portion of the Y-connect feature providing fluid communication between a branch point of the Y-connect feature and a negative pressure source of the pump assembly.

Embodiment 24. The negative pressure wound therapy system of Embodiment 23, wherein the Y-connect feature further comprises a first branch portion and a second branch portion, the first branch portion providing fluid communication between the branch point and an opposite end of the first branch portion, the second branch portion providing fluid communication between the branch point and an opposite end of the second branch portion, wherein the connector port comprises a first connector port and a second connector port, the first connector port disposed at the opposite end of the first branch portion, the second connector port disposed at the opposite end of the second branch portion.

Embodiment 25. The negative pressure wound therapy system of Embodiment 24, further comprising a canister-less-mode dressing configured to be connected to the first connector port.

Embodiment 26. The negative pressure wound therapy system of Embodiment 24 or 25, further comprising a canister-mode dressing configured to be connected to the second connector port.

Embodiment 27. The negative pressure wound therapy system of any one of Embodiments 24-26, further comprising a first valve disposed in the first branch portion and a second valve disposed in the second branch portion, wherein the first valve and second valve are controlled using operational parameters of the pump assembly based on the wound dressings connected to the first and second connector ports.

Embodiment 28. The negative pressure wound therapy system of any one of the preceding Embodiments, comprising a first connector port and a second connector port, the first connector port being in fluid communication with a negative pressure source of the pump assembly, the second connector port being in fluid communication with an irrigation source of the pump assembly.

Embodiment 29. The negative pressure wound therapy system of Embodiment 28, wherein the pump assembly is configured to not operate in the absence of an appropriate connector being connected to each of the first and second connector ports.

Embodiment 30. The negative pressure wound therapy system of Embodiment 28 or 29, wherein delivery of negative pressure and delivery of irrigation is controlled using operational parameters of the pump assembly based on the wound dressings connected to the first and second connector ports.

Embodiment 31. The negative pressure wound therapy system of any one of the preceding Embodiments, further comprising a dual lumen conduit that provides a flow path between the connector and the wound dressing, wherein a first lumen of the dual lumen conduit is configured to provide negative pressure to the wound dressing and the second lumen is configured as a pressure sensing lumen or to provide a vent to the wound dressing.

Embodiment 32. The negative pressure wound therapy system of any one of the preceding Embodiments, wherein the pump assembly is configured to adjust an alarm setting based on an identity of the connector connected to the pump assembly.

Embodiment 33. The negative pressure wound therapy system of any one of the preceding Embodiments, wherein the connector is configured to inform the pump assembly of a compliance requirement for the wound dressing associated with the connector.

Embodiment 34. The negative pressure wound therapy system of Embodiment 33, wherein the pump assembly is configured to indicate when the compliance requirement is not fulfilled.

Embodiment 35. The negative pressure wound therapy system of any one of the preceding Embodiments, further comprising a sensor disposed on the connector or the wound dressing, the sensor being configured to send to the pump assembly a signal that modifies an operational parameter or an alarm setting of the pump assembly.

Embodiment 36. The negative pressure wound therapy system of any one of the preceding Embodiments, wherein the pump assembly is further configured to receive therapy data from an intermediary server upon the connector being connected to the pump assembly, the therapy data modifying one or more operational settings of the pump assembly.

Embodiment 37. The negative pressure wound therapy system of any one of the preceding Embodiments, wherein the pump assembly is further configured transmit identity data from the pump assembly to an intermediary server upon the connector being connected to the pump assembly, the identity data informing the intermediary server of an identity of the connector that is connected to the pump assembly.

Embodiment 38. The negative pressure wound therapy system of any one of the preceding Embodiments, wherein the connector comprises a power source and an alert system, the power source configured to provide power to the alert system when the connector is disconnected from the pump assembly.

Embodiment 39. A method of providing negative pressure wound therapy, the method comprising:
connecting a connector of a wound dressing to a connector port of a pump assembly;
determining one or more characteristics of the wound dressing or a component associated with the wound dressing, wherein determining is performed automatically by the pump assembly;
selecting an operational parameter of the pump assembly based on connecting the connector associated with the wound dressing to the connector port, wherein selecting is performed automatically by the pump assembly; and operating the pump assembly according to the operational parameter.

Embodiment 40. The method of Embodiment 39, wherein the operational parameter is selected from the group consisting of: a negative pressure level, a time duration of the negative pressure level, a temporal variation of the negative pressure level, a volume of fluid infused into the wound, a pressure of a fluid infused into the wound, and an alarm setting.

Embodiment 41. A method of providing negative pressure wound therapy using the negative pressure wound therapy system of any one of Embodiments 1-38.

Embodiment 42. A negative pressure wound therapy system comprising one or more features of the foregoing description.

Embodiment 43. A system comprising a medical device and a patient-contacting disposable, the system comprising one or more features of the foregoing description.

Embodiment 44. A method of operating a medical device comprising one or more features of the foregoing description.

Embodiment 45. A connector or dongle comprising one or more features of the foregoing description.

Embodiment 46. A negative pressure wound therapy kit comprising:
a pump assembly;
a connector port disposed on the pump assembly, the connector port configured to receive a connector associated with a wound dressing; and
a dongle configured to communicate with the pump assembly;
wherein the dongle is configured to automatically adjust an operational parameter of the pump assembly.

Embodiment 47. The negative pressure wound therapy kit of Embodiment 46, wherein the pump assembly further comprises a dongle port disposed on the pump assembly, wherein the dongle port is configured to receive the dongle.

Embodiment 48. A device activation system comprising a dongle, wherein the dongle is configured to communicate data to a medical device, wherein one or more operational parameters of the medical device is modified in response to the medical device receiving the data from the dongle.

Embodiment 49. The device activation system of Embodiment 48, wherein the dongle is configured to transmit the data to the medical device through a wired connection that is formed by plugging the dongle into a dongle port disposed on the medical device.

Embodiment 50. The device activation system of Embodiment 48, wherein the dongle is configured to transmit the data to the medical device through a wireless connection formed by swiping the dongle over a dongle reader disposed on the medical device.

Embodiment 51. The device activation system of Embodiment 48, wherein the dongle is configured to connect to a connector disposed on a patient-contacting disposable, wherein the medical device comprises a connector port configured to receive at least a portion of an assembly formed by connecting the dongle to the connector.

What is claimed is:
1. A negative pressure wound therapy system comprising:
a negative pressure source configured to provide negative pressure to a wound covered by a wound dressing;
a housing supporting the negative pressure source;
a connector port supported by the housing, the connector port configured to receive a dressing connector associated with a first wound dressing or a second wound dressing; and
a controller configured to operate the negative pressure source, the controller further configured to:
automatically cause the negative pressure source to provide to the first wound dressing a first negative pressure level associated with the first wound dressing responsive to the connector port receiving the dressing connector associated with the first wound dressing; and
automatically cause the negative pressure source to provide to the second wound dressing a second negative pressure level associated with the second wound dressing responsive to the connector port receiving the dressing connector associated with the second wound dressing, wherein the first negative pressure level associated with the first wound dressing is different than the second negative pressure level associated with the second wound dressing.

2. The negative pressure wound therapy system of claim 1, wherein the controller is further configured to:
 initiate a first lifetime timer for the negative pressure source responsive to the connector port receiving the dressing connector associated with the first wound dressing or the second wound dressing; and
 power off the negative pressure source responsive to the first lifetime timer satisfying a first threshold indicative of a first lifespan of the negative pressure source when the dressing connector associated with the first wound dressing is received by the connector port or responsive to the first lifetime timer satisfying a second threshold indicative of a second lifespan of the negative pressure source when the dressing connector associated with the second wound dressing is received by the connector port;
 wherein the first lifespan is different than the second lifespan.

3. The negative pressure wound therapy system of claim 2, wherein the controller is further configured to initiate a second lifetime timer for the first wound dressing or a third lifetime timer for the second wound dressing responsive to the connector port receiving the dressing connector associated with the first wound dressing or the second wound dressing, respectively.

4. The negative pressure wound therapy system of claim 3, wherein the controller is further configured to power off the negative pressure source responsive to the second lifetime timer satisfying a third threshold indicative of a lifespan of the first wound dressing or the third lifetime timer satisfying a fourth threshold indicative of a lifespan of the second wound dressing, and wherein the third threshold is different than the fourth threshold.

5. The negative pressure wound therapy system of claim 1, wherein the controller is further configured to:
 automatically set or adjust a first alarm setting associated with the first wound dressing responsive to the connector port receiving the dressing connector associated with the first wound dressing; and
 automatically set or adjust a second alarm setting associated with the second wound dressing responsive to the connector port receiving the dressing connector associated with the second wound dressing,
 wherein the first alarm setting associated with the first wound dressing is different than the second alarm setting associated with the second wound dressing.

6. The negative pressure wound therapy system of claim 1, wherein the controller is further configured to automatically power on the negative pressure source responsive to the connector port receiving the dressing connector associated with the first wound dressing or the second wound dressing.

7. The negative pressure wound therapy system of claim 1, wherein the controller is further configured to upload data to a computer server responsive to the dressing connector associated with the first wound dressing or the second wound dressing being disconnected from the connector port.

8. The negative pressure wound therapy system of claim 1, further comprising a user interface supported by the housing, wherein the controller is configured to automatically select a first available option of the user interface based on the connector port receiving the dressing connector associated with the first wound dressing or a second available option of the user interface based on the connector port receiving the dressing connector associated with the second wound dressing, and wherein the first available option is different than the second available option.

9. The negative pressure wound therapy system of claim 1, wherein the controller is further configured to:
 automatically provide to the first wound dressing a first duration of negative pressure associated with the first wound dressing responsive to the connector port receiving the dressing connector associated with the first wound dressing; and
 automatically provide to the second wound dressing a second duration of negative pressure associated with the second wound dressing responsive to the connector port receiving the dressing connector associated with the second wound dressing,
 wherein the first duration of negative pressure associated with the first wound dressing is different than the second duration of negative pressure associated with the second wound dressing.

* * * * *